United States Patent [19]

Uchida et al.

[11] Patent Number: 5,190,686
[45] Date of Patent: Mar. 2, 1993

[54] LIQUID-CRYSTALLINE COPOLYMER

[75] Inventors: Shunji Uchida; Satoshi Hachiya; Kenji Hashimoto, all of Chiba, Japan

[73] Assignee: Idemitsu Kosan Co., Ltd., Tokyo, Japan

[21] Appl. No.: 395,058

[22] Filed: Aug. 17, 1989

[30] Foreign Application Priority Data

Aug. 26, 1988 [JP] Japan .................. 63-210659
Sep. 5, 1988 [JP] Japan .................. 63-220411

[51] Int. Cl.$^5$ .................. C09K 19/52; C08G 59/00; C08G 65/08
[52] U.S. Cl. .................. 252/299.01; 528/100; 528/421; 528/105
[58] Field of Search .................. 252/299.01; 528/84, 528/100, 105, 361, 362, 421

[56] References Cited

U.S. PATENT DOCUMENTS

| | | | |
|---|---|---|---|
| 4,615,586 | 10/1986 | Geary et al. | 350/350 S |
| 4,877,858 | 10/1989 | Hachiya et al. | 528/100 |
| 4,943,387 | 7/1990 | Furukawa et al. | 252/299.67 |
| 5,037,186 | 8/1991 | Itoh et al. | 252/299.01 |

FOREIGN PATENT DOCUMENTS

| | | |
|---|---|---|
| 0136725 | 4/1985 | European Pat. Off. |
| 0227419 | 7/1987 | European Pat. Off. |
| 0274128 | 7/1988 | European Pat. Off. |
| 0297554 | 1/1989 | European Pat. Off. |

OTHER PUBLICATIONS

Patent Abstracts of Japan, vol. 13, No. 72.
Proceedings of the Society for Information Display (SID), vol. 28, No. 2, pp. 167–174.

*Primary Examiner*—Robert L. Stoll
*Assistant Examiner*—Shean C. Wu
*Attorney, Agent, or Firm*—Antonelli, Terry, Stout & Kraus

[57] ABSTRACT

A liquid-crystalline copolymer having a long helical pitch, the liquid-crystalline copolymer comprises the copolymerization product of;
(a) at least one liquid-crystalline epoxy compound having a helical structure and
(b) at least one liquid-crystalline epoxy compound having a helical structure opposite in twining direction of helix to the helical structure of the liquid-crystalline epoxy compound (a) or
(c) at least one non-liquid-crystalline epoxy compound.

14 Claims, 14 Drawing Sheets

LIQUID-CRYSTALLINE COPOLYMER

BACKGROUND OF THE INVENTION (a) Field of the Invention

The present invention relates to a novel liquid-crystalline copolymer. More specifically, the present invention relates to a novel liquid-crystalline copolymer which exhibits ferroelectricity even at temperatures around room temperature, has a long helical pitch, and has such a high speed of response to external factors as to enable display of motion pictures. Such a liquid-crystalline copolymer is useful in optoelectronics fields as various kinds of optical elements, particularly, as those for display devices for desk calculators, clocks and watches, etc., and those for various electronic optical devices for electronic optical shutters, electronic optical diaphragms, optical modulators, optical-path transfer switches in optical communication systems, memories, liquid crystal printer heads, varifocal lenses, etc. In particular, the liquid-crystalline copolymer of the present invention has a high practicality in its use as the display elements for large display screens or curved display screens.

(b) Description of the Related Art

Display devices in which low molecular weight liquid crystals are used as the display element have been widely used for digital display of desk calculators, clocks and watches, etc. In these fields of utilization, the conventional low molecular weight liquid crystals are generally supported between a couple of glass substrates spaced from each other in microns. However, such an adjustment of the space has been practically impossible in production of large display screens or curved display screens. In order to solve the problem, some attempts have been made to develop polymeric liquid crystals so as to render moldability to the liquid crystals themselves. For example, in Japanese Patent Application Kokai Koho No. 55-21479, Japanese Patent Application Kokai Koho No. 63-99204, and EP-0184482 disclosed are various kinds of polyacrylate-type ferroelectric polymeric liquid crystals. Nevertheless, these conventional polymeric liquid crystals have hardly been satisfactory for practical use because of their high temperature ranges where ferroelectricity is exhibited. Further, these polymeric liquid crystals have deficiencies in that their speeds of response in the changes of their transmission intensity to the changes of external factors such as electric field are generally slow and sufficient bistability cannot be attained because of their short helical pitches.

Since ferroelectric liquid crystals exhibiting chiral smectic C phase (SmC* phase) have a layered structure and the director 'n' of the molecules gradually rotates about the normal line of the layers with each layer, the directors 'n' of the molecules on the whole construct a helical structure. The distance between the planes perpendicular to the helical axis required by the director to rotate for 360° is called helical pitch. For instance, DOBAMBC has a helical pitch of from 2 to 3 μm which, considering the size of the molecule, indicates that one pitch consists of molecule layers close to 1000. In comparison with the conventional nematic liquid crystals, ferroelectric liquid crystals are characteristically used as the materials of display devices because of their high speed response property and bistability (memory property). There exists a close connection between bistability and the helical pitch of ferroelectric liquid crystals, and, in order to obtain a display device having bistability, it is necessary to make the cell gap 'd' smaller than the helical pitch 'p' so that the ferroelectric liquid crystal operates at a state with its helix loosened. For this reason, there has been a demand for development of ferroelectric liquid crystal materials having long helical pitches.

SUMMARY OF THE INVENTION

Accordingly, the object of the present invention is to provide a liquid crystal polymer which not only exhibits ferroelectricity even at temperatures neighboring room temperature but also has high speed of response to external factors enabling display of motion pictures and, as well, can be advantageously used as the display element for display devices having a large display screen or curved screen.

As the result of repeated researches for solving the above problems, we found that a liquid-crystalline copolymer obtainable by copolymerizing two liquid-crystalline epoxy monomers having specified structures and being opposite in twining direction of helix to each other or by copolymerizing a liquid-crystalline epoxy monomer and a non-liquid-crystalline epoxy monomer exhibits a high speed response within a wide temperature range neighboring room temperature and has a long helical pitch, and we eventually completed the present invention.

Thus, the present invention provides a liquid-crystalline copolymer comprising the copolymerization product of;

(a) at least one liquid-crystalline epoxy compound having a helical structure and (b) at least one liquid-crystalline epoxy compound having a helical structure opposite in twining direction of helix to the helical structure of the liquid-crystalline epoxy compound (a) or (c) at least one non-liquid-crystalline epoxy compound.

DESCRIPTION OF THE PREFERRED EMBODIMENTS

Figure 1:
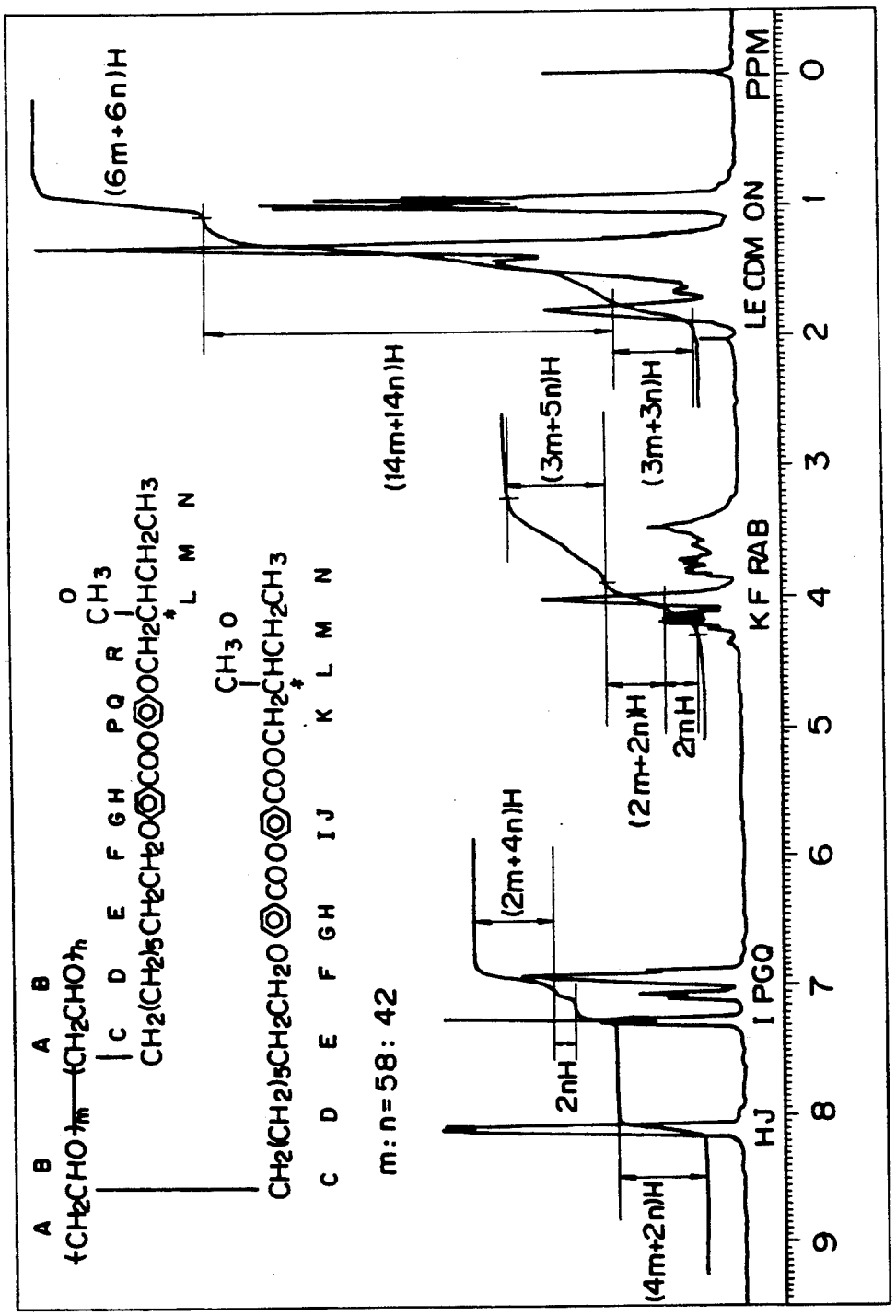
FIG. 1 is a chart showing an NMR spectrum of the liquid-crystalline copolymer prepared in Example 1.

One of the preferred embodiments of the liquid-crystalline copolymers of the present invention is a liquid-crystalline copolymer comprising the copolymerization product of;
(a) at least one liquid-crystalline epoxy compound which has a helical structure and is represented by the following general formula (1) and
(b) at least one liquid-crystalline epoxy compound which has a helical structure opposite in twining direction of helix to the helical structure of the liquid-crystalline epoxy compound (a) and is represented by the following general formula (2),
the copolymerization product comprising at least one repeating unit represented by the following general formula (3) and at least one repeating unit represented by the following general formula (4), wherein the molar ratio of the repeating unit (3) to the repeating unit (4) is from 99:1 to 1:99;

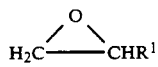  (1)

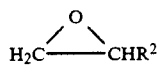  (2)

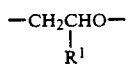  (3)

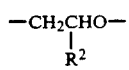  (4)

wherein $R^1$ and $R^2$ are different from each other and each independently are a group represented by —(CH$_2$)$_k$—OR$^3$, wherein
k is an integer having a value of from 1 to 30,
$R^3$ is a group represented by —A$_p$—X—B$_q$—R$^4$, wherein
X is a single bond, —COO— or —OCO—,
p and q each independently are an integer having a value of 1 or 2,
A is

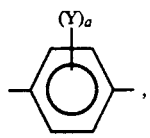

B is

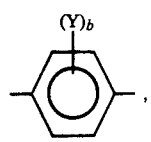

a and b each independently being an integer having a value of from 0 to 4 and being identical with or different from each other, each Y being a halogen atom and being identical with or different from the others,
A and B are identical with or different from each other, and
$R^4$ is —COOR$^5$, —OCOR$^5$ or —OR$^5$, wherein $R^5$ is

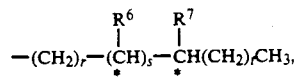

$R^6$ and $R^7$ each independently being —CH$_3$, a halogen atom, —CN or —CF$_3$, r and t each independently being an integer having a value of from 0 to 10, with the proviso that t is not 0 when $R^7$ is —CH$_3$, s being an integer of 0 or 1, and C marked with * being an asymmetric carbon atom.

Liquid-crystalline molecules exhibiting a chiral smectic phase or chiral nematic phase construct a helical structure, and the twining direction of the helical structure (clockwise twining: R, anticlockwise twining: L) depends on the structure of the optically active group, the type of the stereoisomerism of the asymmetric carbon atoms in the optically active group (i.e., R configuration or S configuration), the distance of from the skeletal portion to the asymmetric carbon atom in the optically active group, and so on. Copolymerization of two monomers whose structure molecules are opposite in twining direction of helix to each other provides a liquid-crystalline copolymer in which two kinds of copolymer units opposite in twining direction of helix to each other exist together. In this liquid-crystalline copolymer, the helical properties of the two kinds of copolymer units compensate each other, resulting in an extended helical pitch of the copolymer. The extended helical pitch makes it unnecessary to adjust the thickness of liquid crystal cells accurately to about 1 to 2 μm, thereby offering an advantage in preparation of devises.

In the above formula, k is an integer having a value of from 1 to 30, and the preferred value is from 4 to 16. The preferred value of r is 0 to 2.

In the above formula, some illustrative examples of A and B include the groups represented by the following formulas, respectively:

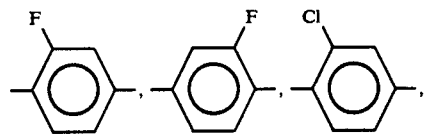

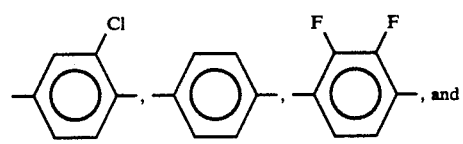, and

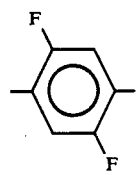

Typical examples of $R^3$ include

—⟨◯⟩—COO—⟨◯⟩—COOR⁵,

—⟨◯⟩—COO—⟨◯⟩—OR⁵,

—⟨◯⟩—⟨◯⟩—COO—⟨◯⟩—COOR⁵,

—⟨◯⟩—COO—⟨◯⟩—⟨◯⟩—COOR⁵,

—⟨◯⟩—COO—⟨◯⟩(F)—COOR⁵,

—⟨◯⟩—COO—⟨◯⟩—OCOR⁵, and

—⟨◯⟩—⟨◯⟩—COOR⁵.

In the above formulas, some illustrative examples of the optically active group $R^5$ include 2-methylbutyl group, 2-fluorooctyl group, 2-chloro-1-methylpropyl group, 2-cyanobutyl group, 1-(trifluoromethyl)heptyl group, 1-methylpropyl group, 1-methylbutyl group, 3-methylpentyl group, and 3-chloro-2-methylpentyl group.

Among various applicable combinations of $R^1$ and $R^2$, some examples of the preferred combinations include a combination of $R^1$ wherein $R^4$ is $$-COO-CH_2\overset{*}{C}HC_2H_5 \quad (CH_3) \text{ and}$$

$R^2$ wherein $R^4$ is $$-COO-\overset{*}{C}H(CH_2)_tCH_3, \quad (CH_3)$$

t being preferably an integer having a value of 2 to 5 and a combination of $R^1$ wherein $R^4$ is $$-COO-CH_2\overset{*}{C}HC_2H_5 \quad (CH_3) \text{ and}$$

$R^2$ wherein $R^4$ is $$-COO-CH_2\overset{*}{C}H(CH_2)_tCH_3, \quad (F)$$

t being preferably an integer having a value of from 3 to 5.

Further, in order to facilitate controlling the temperature ranges of liquid crystal phases, it is preferable to use one liquid-crystalline epoxy compound having a two-cyclic structure and the other liquid-crystalline epoxy compound having a three-cyclic structure, in combination.

As the liquid-crystalline epoxy compounds represented by the formulas (1) and (2) to be used for preparation of the copolymerization product in the present invention, a combination of those opposite in twining direction of helix to each other is used.

Typical examples of the liquid-crystalline epoxy compound having R configuration (clockwise twining) include

H₂C(O)CH(CH₂)₈O—⟨◯⟩—⟨◯⟩—COOCH₂C*HC₂H₅ (CH₃), (S)

H₂C(O)CH(CH₂)₆O—⟨◯⟩—COO—⟨◯⟩—⟨◯⟩—COOCH₂C*HC₂H₅ (CH₃), (S)

H₂C(O)CH(CH₂)₈O—⟨◯⟩—COO—⟨◯⟩(F)—COOC*H(CH₂)₅CH₃ (CF₃), (R)

H₂C(O)CH(CH₂)₈O—⟨◯⟩—COO—⟨◯⟩—COOCH₂C*HC₂H₅ (CH₃), (S)

-continued

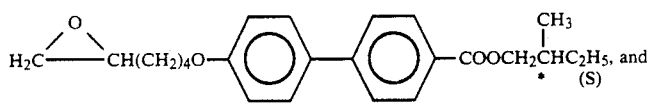

and typical examples of the liquid-crystalline epoxy compound having L configuration (anticlockwise twining) include

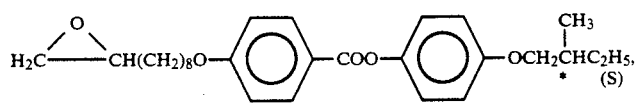

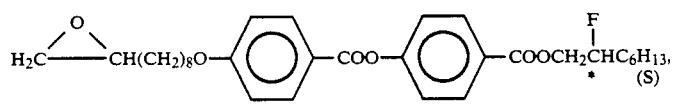

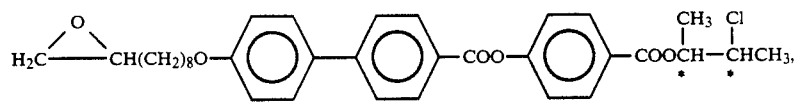

(The absolute configuration is not known.)

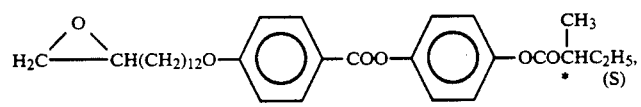

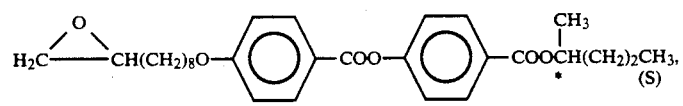

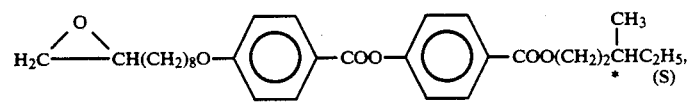

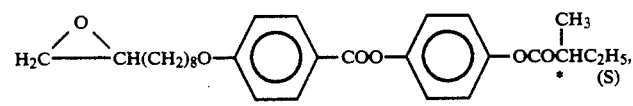

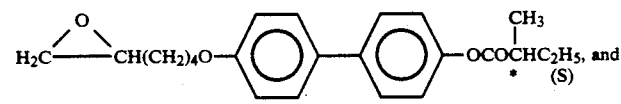

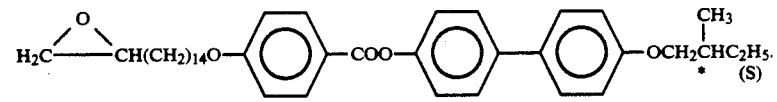

At least one epoxy compound of R configuration and at least one epoxy compound of L configuration, for example, those shown above, are combined properly to be copolymerized so that the molar ratio of the repeating unit (3) to the repeating unit (4) becomes from 99:1 to 1:99, preferably from 80:20 to 20:80. If the molar ratio deviates from the range of from 99:1 to 1:99, the effect of extending the helical pitch cannot be expected.

The preferred number average molecular weight of the liquid-crystalline copolymer is from 1,000 to 500,000. If the number average molecular weight is less than 1,000, the moldability of the copolymer into film or coated film will be occasionally deteriorated. If it is more than 500,000, there will occasionally appear undesirable effects such as lowered response speed. Although the particularly preferred range of the number average molecular weight cannot be defined uniformly since it depends on the kinds of $R^1$ and $R^2$, the numerical value of k, the optical purity of $R^5$, etc., it is generally from 1,000 to 200,000.

Another preferred embodiment of the liquid-crystalline copolymers of the present invention is a liquid-crystalline copolymer comprising the copolymerization product of;
(a) at least one liquid-crystalline epoxy compound which has a helical structure and is represented by the following general formula (1) and
(c) at least one non-liquid-crystalline epoxy compound represented by the following general formula (5),
the copolymerization product comprising at least one repeating unit represented by the following general formula (3) and at least one repeating unit represented by the following general formula (6), wherein the molar ratio of the repeating unit (3) to the repeating unit (6) is from 99:1 to 10:90;

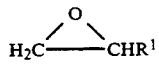 (1)

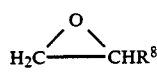 (5)

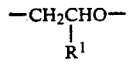 (3)

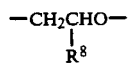 (6)

wherein $R^1$ is a group represented by $-(CH_2)_k-OR^3$, wherein
k is an integer having a value of from 1 to 30,
$R^3$ is a group represented by $-A_p-X-B_q-R^4$, wherein
X is a single bond, $-COO-$ or $-OCO-$,
p and q each independently are an integer having a value of 1 or 2,
A is

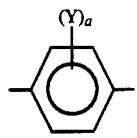

B is

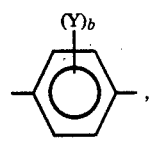

a and b each independently being an integer having a value of from 0 to 4 and being identical with or different from each other, each Y being a halogen atom and being identical with or different from the others,
A and B are identical with or different from each other, and
$R^4$ is $-COOR^5$, $-OCOR^5$ or $-OR^5$, wherein $R^5$ is

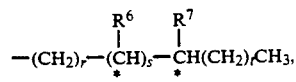

$R^6$ and $R^7$ each independently being $-CH_3$, a halogen atom, $-CN$ or $-CF_3$, r and t each independently being an integer having a value of from 0 to 10, with the proviso that t is not 0 when $R^7$ is $-CH_3$, s being an integer of 0 or 1, and C marked with * being an asymmetric carbon atom; and
$R^8$ is $-H$ or a group represented by $-(CH_2)_u CH_3$, u being an integer having a value of from 0 to 9.

That is, copolymerization of a liquid-crystalline monomer having a helical structure with an epoxy monomer without helical structure provides a liquid-crystalline copolymer in which a copolymer unit having a helical structure and a copolymer unit without helical structure coexist. In this copolymer, the helical properties of the copolymer unit having a helical structure is weakened by the dilution effect of the copolymer unit without helical structure, resulting in an extended helical pitch of the resulting copolymer. At the same time, the presence of the non-liquid-crystalline copolymer unit enables the ferroelectric phase temperature range of a liquid-crystalline polymer exhibiting, in itself, ferroelectric phase at a higher temperature range to be lowered to a temperature neighboring room temperature.

The liquid-crystalline copolymer can be prepared by copolymerizing a combination of at least one monomer represented by the general formula (1) and at least one monomer represented by the general formula (5) so that the molar ratio of the repeating unit represented by the general formula (3) to the repeating unit represented by the general formula (6) becomes from 99:1 to 10:90, preferably from 90:10 to 20:80. If the molar ratio deviates from the range of from 99:1 to 10:90, there cannot be expected extension of the helical pitch nor sufficiently high speed response.

The preferred number average molecular weight of the liquid-crystalline copolymer described above is from 1,000 to 500,000. If the number average molecular weight is less than 1,000, the moldability of the copolymer into film or coated film will be occasionally deteriorated. If it is more than 500,000, there will occasionally appear undersirable effects such as lowered response speed. Although the particularly preferred range of the number average molecular weight cannot be defined uniformly since it depends on the kinds of $R^1$ and $R^8$, the numerical values of k and u, the optical purity of $R^5$, etc., it is generally from 1,000 to 200,000.

Hereinafter, there will be described general methods of synthesizing the liquid-crystalline epoxy compounds to be used as the monomers (1) and (2) for the liquid-crystalline copolymer of the present invention.
(1) In the case that $R^3$ is

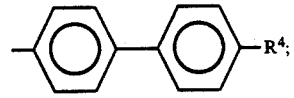

(A=

B =
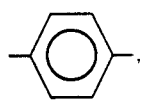,

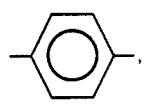,

X=single bond, p and q=1)

As shown by the following reaction formulas, at first, an alkenol (I) is halogenized with a halogenizing agent, such as thionyl chloride, in the presence of pyridine, to obtain an alkene halide (II). The alkene halide (II) is reacted with a compound (III) in a proper solvent, such as 2-butanone, in the presence of an alkali, such as potassium carbonate, to obtain an ether compound (IV). Subsequently, the ether compound (IV) is epoxidized with a per acid, such as m-chloroperbenzoic acid, in a proper solvent, such as dichloromethane, to obtain the objective monomer (V).

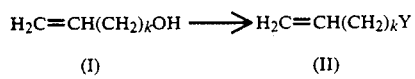

(I)    (II)

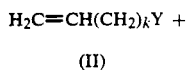

(II)

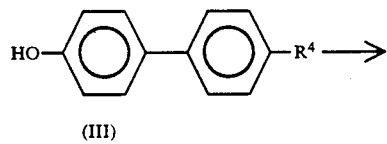

(III)

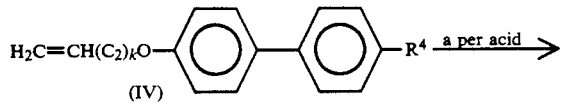

(IV)

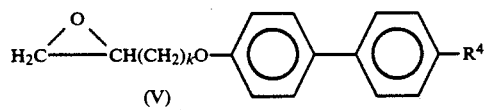

(V)

(In the above formulas, Y is a halogen atom.)

The preferred examples of the alkenol (I) include 9-decene-1-ol, 11-dodecene-1-ol, 7-octene-1-ol, and 13-tetradecene-1-ol.

The above described compound (III),

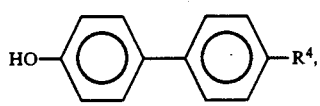

can be synthesized as follows.

Synthesis of

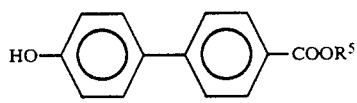

As shown by the following reaction formula, the objective ester compound (VII) is prepared by reacting 4'-hydroxybiphenyl-4-carboxylic acid with an optically active alcohol (VI) in a proper solvent, such as benzene, at a desired temperature, in the presence of an esterification catalyst, such as concentrated sulfuric acid or p-toluenesulfonic acid.

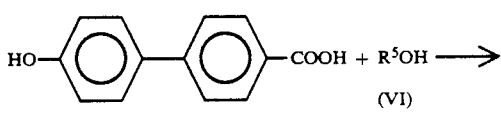

(VI)

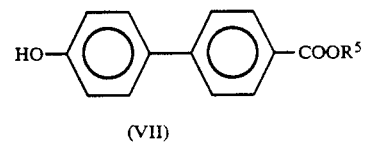

(VII)

Some illustrative examples of the optically active alcohol (VI) which may be used include (R)-2-methylbutanol, (S)-2-methylbutanol, (R)-4-methylhexanol, (S)-4-methylhexanol, (R)-2-chloropropanol, (S)-2-chloropropanol, (R)-2-cyanopropanol, (S)-2-cyanopropanol, (R)-4-chloropentanol, (S)-4-chloropentanol, (R)-2-butanol, (S)-2-butanol, (S)-2-pentanol, (R)-2-pentanol, (S)-2-octanol, (R)-2-octanol, (S)-2-fluorooctanol, (R)-2-fluorooctanol, (S)-2-fluorononanol, (R)-2-fluorononanol, (2S, 3S)-2-chloro-3-methyl-1-pentanol, (2S, 3S)-2-fluoro-3-methyl-1-pentanol, (2S, 3S)-2-bromo-3-methyl-1-pentanol, (3S, 4S)-3-chloro-4-methyl-1-hexanol, (4S, 5S)-4-chloro-5-methyl-1-heptanol, (5S, 6S)-5-chloro-6-methyl-1-octanol, (6S, 7S)-6-chloro-7-methyl-1nonanol, (R)-(+)-1,1,1-trifluoro-2-octanol, 3-chloro-2-butanol, and (S)-(+)-3-methylpentanol.

Synthesis of

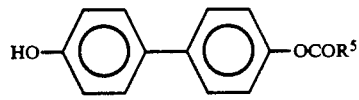

As shown by the following reaction formula, the objective ester compound (IX) may be prepared by reacting biphenyl-4,4'-diol with an optically active carboxylic acid (VIII).

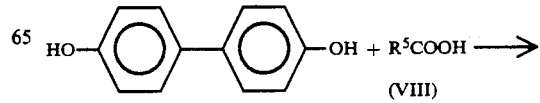

(VIII)

-continued

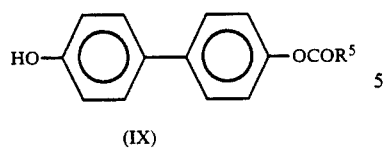

(IX)

Some illustrative examples of the optically active carboxylic acid (VIII) which may be used include (R)-2-methylbutanoic acid, (S)-2-methylbutanoic acid, (2S, 3S)-2-chloro-3-methylpentanoic acid, (2S, 3S)-2-fluoro-3-methylpentanoic acid, (R)-2-methylpentanoic acid, (S)-2-methylpentanoic acid, (R)-3-methylpentanoic acid, (S)-3-methylpentanoic acid, (R)-4-methylhexanoic acid, (S)-4-methylhexanoic acid, (R)-2-chloropropanoic acid, (S)-2-chloropropanoic acid, (R)-6-methyloctanoic acid, (S)-6-methyloctanoic acid, (R)-2-cyanobutanoic acid, (S)-2-cyanobutanoic acid, (R)-2-cyanopropanoic acid, and (S)-2-cyanopropanoic acid.

Synthesis of

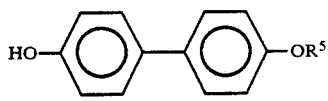

As shown by the following reaction formulas, the above-described optically active alcohol (VI) is tosylated and then reacted with biphenyl-4,4'-diol, to obtain the objective ether compound (X).

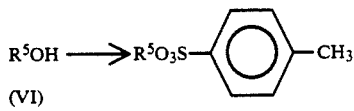

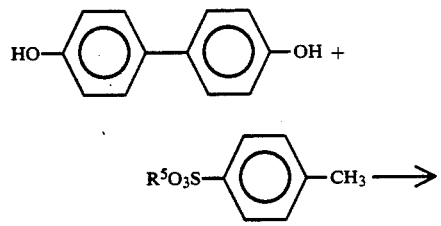

-continued

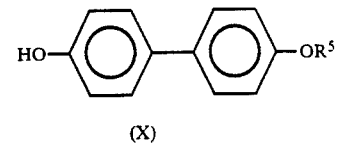

(X)

(2) In the case that $R^3$ is

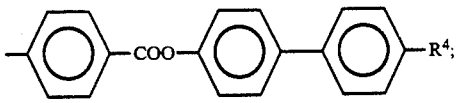

(A =

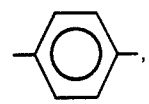,

B =

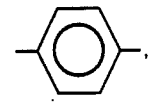,

X = —COO—, p = 1, q = 2)

As shown by the following reaction formulas, at first, an alkene halide (II) is reacted with ethyl p-hydroxybenzoate in a proper solvent, such as acetone, in the presence of an alkali, such as potassium carbonate, to obtain an ether compound. Subsequently, the group protecting the carboxyl group in the ether compound is eliminated by using an aqueous potassium hydroxide solution, hydrochloric acid, etc., to obtain an carboxylic acid compound. The carboxylic acid is converted into an acid halide by adding a halogenating agent, such as thionyl chloride, and heating the obtained mixture in a solvent, such as toluene. The acid halide is reacted with the above-described compound (III) in a solvent, such as toluene, in the presence of pyridine, to obtain an ester compound (XI), and the obtained ester compound (XI) is epoxidized in a proper solvent, such as dichloromethane, by using a per acid, such as m-chloroperbenzoic acid, to obtain the objective monomer (XII).

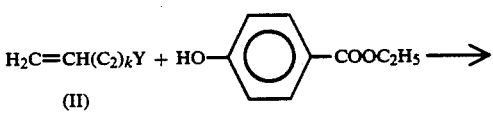

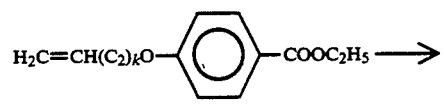

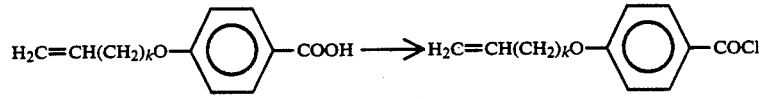

$H_2C=CH(CH_2)_kO-\bigcirc-COCl + HO-\bigcirc-\bigcirc-R^4 \longrightarrow$ (III)

$H_2C=CH(CH_2)_kO-\bigcirc-COO-\bigcirc-\bigcirc-R^4 \xrightarrow{\text{a per acid}}$ (XI)

$H_2C\overset{O}{\underset{\diagdown}{-}}CH(CH_2)_kO-\bigcirc-COO-\bigcirc-\bigcirc-R^4$ (3) In the case that $R^3$ is $-\bigcirc-COO-\bigcirc-\bigcirc-R^4;$ (A = $-\bigcirc-$, B = $-\bigcirc-$, X = —OCO—, p=1, q=2)

As shown by the following reaction formulas, at first, an alkene halide (II) is reacted with hydroquinone in the presence of an alkali, such as potassium carbonate, to obtain an ether compound (XIII).

The compound (XIV) described below is converted into an acid chloride with thionyl chloride or the like. The obtained acid chloride is reacted with the ether compound (XIII) in the presence of pyridine, to obtain an ester compound (XV). After this, epoxidation is carried out in the same manner as in the case (1), to obtain the objective monomer (XVI).

$H_2C=CH(CH_2)_kY + HO-\bigcirc-OH \longrightarrow$ (II)

$H_2C=CH(CH_2)_kO-\bigcirc-OH$ (XIII)

$HOOC-\bigcirc-\bigcirc-R^4 \xrightarrow{SOCl_2}$ (XIV)

$ClCO-\bigcirc-\bigcirc-R^4 \xrightarrow{XIII}$ $H_2C=CH(CH_2)_kO-\bigcirc-OCO-\bigcirc-\bigcirc-R^4 \xrightarrow{\text{a per acid}}$ (XV)

$H_2C\overset{O}{\underset{\diagdown}{-}}CH(CH_2)_kO-\bigcirc-OCO-\bigcirc-\bigcirc-R^4$ (XVI)

The above-described compound (XIV), $HOOC-\bigcirc-\bigcirc-R^4,$ may be prepared as follows.

Synthesis of $HOOC-\bigcirc-\bigcirc-COOR^5$

An optically active alcohol (VI) is reacted with biphenyl-4,4'-dicarboxylic acid in a solvent, such as toluene, in the presence of an esterification catalyst, to obtain the objective ester compound (XVII).

$R^3OH + HOOC-\bigcirc-\bigcirc-COOH \longrightarrow$ (VI)

$HOOC-\bigcirc-\bigcirc-COOR^5$ (XVII)

Synthesis of

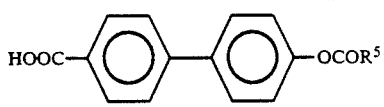

After an optically active carboxylic acid (VIII) is converted into an acid chloride by using thionyl chloride or the like, the obtained acid chloride is reacted with 4'-hydroxybiphenyl-4-carboxylic acid in the presence of pyridine, to obtain the objective ester compound (XVIII).

$$R^5COOH \xrightarrow{SOCl_2} R^5COCl$$
(VIII)

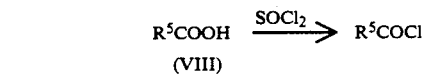

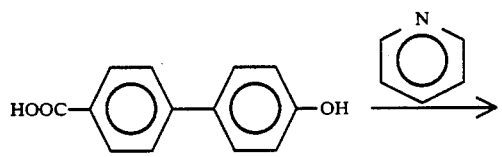

(XVIII)

Synthesis of

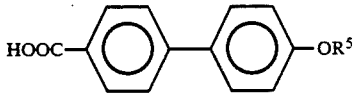

Ethyl 4'-hydroxybiphenyl-4-carboxylate and

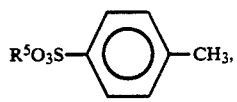

which is prepared by tosylating an optically active alcohol (VI), are reacted in the presence of potassium carbonate or the like, to obtain an ether compound. The obtained ether compound is reacted with an aqueous alkali solution to hydrolyze the ester portion to eliminate the protecting group, and the objective compound (XIX) is obtained.

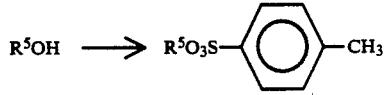

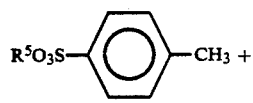

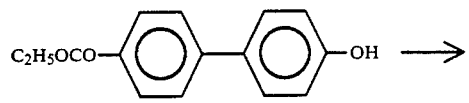

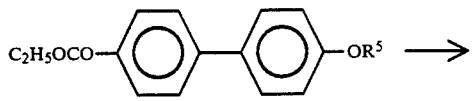

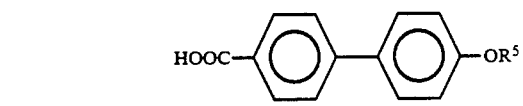

(XIX)

(4) In the case that $R^3$ is

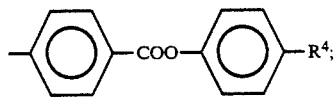

(A =

B =

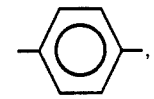

X = —COO—, p = 1, q = 1)

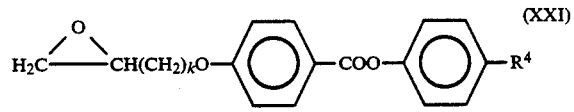

(XXI)

The objective monomer (XXI) may be prepared in the same manner as in the synthetic method (2) for preparing the monomer wherein $R^3$ is

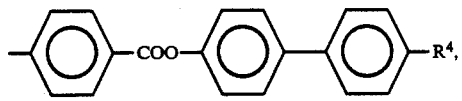

with the exception that the compound (III),

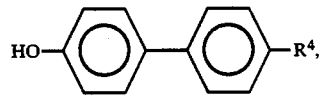

is replaced by a compound (XX),

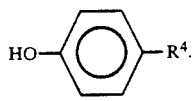

The above-described compound (XX) may be prepared as follows.

Synthesis of

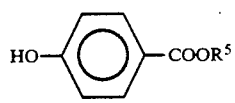

The objective ester compound (XXII) may be prepared in the same manner as in the synthetic method for preparing the compound (VII) in the case (1), with the exception that 4'-hydroxybiphenyl-4-carboxylic acid is replaced by p-hydroxybenzoic acid.

Synthesis of

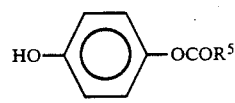

The objective ester compound (XXIII) may be prepared in the same manner as in the synthetic method for preparing the compound (VIII) in the case (1), with the exception that biphenyl-4,4'-diol is replaced by hydroquinone.

Synthesis of

The objective ether compound (XXIV) may be prepared in the same manner as in the synthetic method for preparing the compound (X) in the case (1), with the exception that biphenyl-4,4'-diol is replaced by hydroquinone.

(5) In the case that $R^3$ is

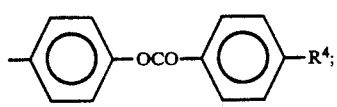

(A=

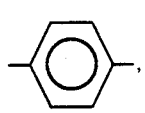

B=

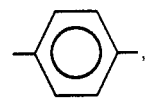

$X = -OCO-$, $p=1$, $q=1$)

As shown by the following reaction formulas, the objective monomer (XXVI) may be prepared in the same manner as in the synthetic method (3) for preparing the monomer wherein $R^3$ is

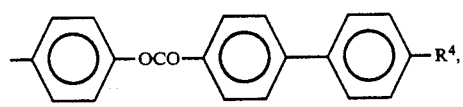

with the exception that the compound (XIV),

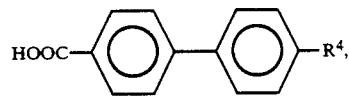

is replaced by a compound (XXV),

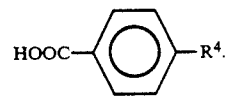

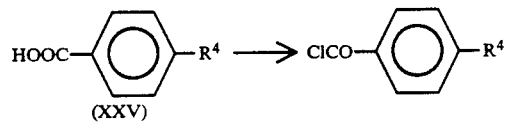

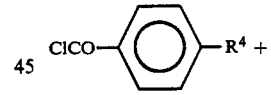

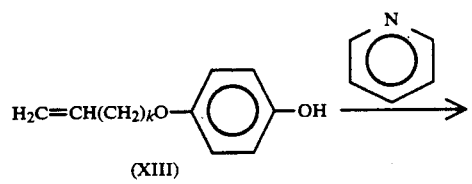

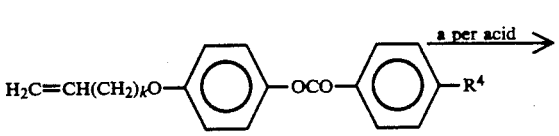

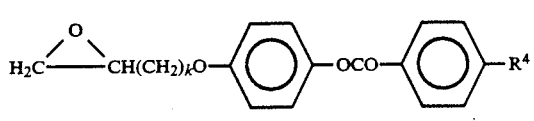

The above-described compound (XXV) may be prepared as follows.

Synthesis of

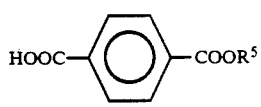

The objective ester compound (XXVII) may be prepared in the same manner as in the synthetic method for preparing the compound (XVII) in the case (3), with the exception that biphenyl-4,4'-dicarboxylic acid is replaced by terephthalic acid.

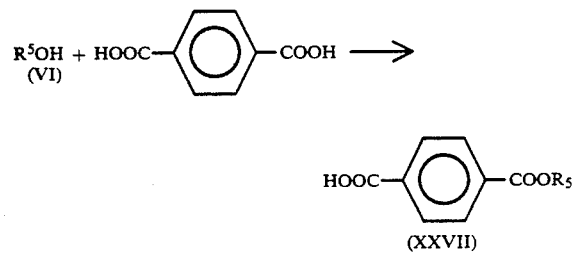

Synthesis of

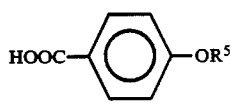

The objective ester compound (XXVIII) may be prepared in the same manner as in the synthetic method for preparing the compound (XVIII) in the case (3), with the exception that 4'-hydroxybiphenyl-4-carboxylic acid is replaced by p-hydroxybenzoic acid.

$R^5COOH \longrightarrow R^5COCl$
(VIII)

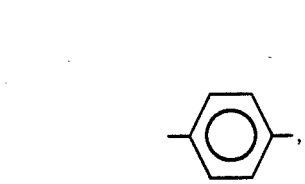

Synthesis of

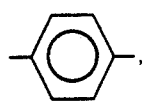

The objective ether compound (XXIX) may be prepared in the same manner as in the synthetic method for preparing the compound (XIV) in the case (3), with the exception that ethyl 4'-hydroxybiphenyl-4-carboxylate is replaced by ethyl p-hydroxybenzoate.

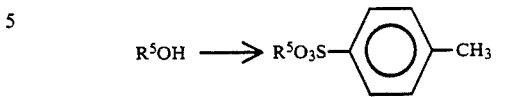

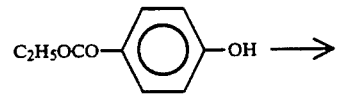

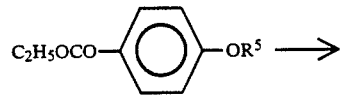

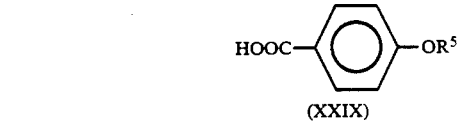

(XXIX)

(6) In the case that $R^3$ is

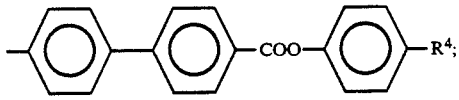

(A =

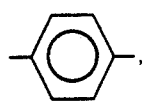,

B =

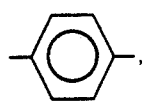,

X = —COO—, p = 2, q = 1)

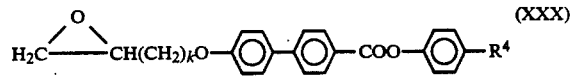
(XXX)

The objective monomer (XXX) may be prepared in the same manner as in the synthetic method (2) for preparing the monomer wherein $R^3$ is

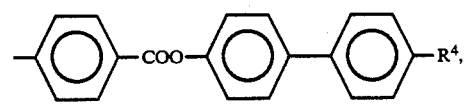

with the exception that ethyl p-hydroxybenzoate is replaced by ethyl 4'-hydroxybiphenyl-4-carboxylate, and the compound (III),

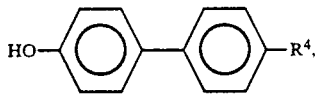

is replaced by a compound (XX),

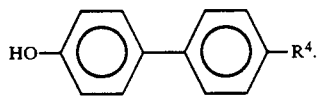

(7) In the case that $R^3$ is

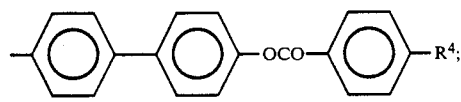

(A =

B =

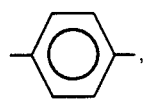

X = —OCO—, p = 2, q = 1)

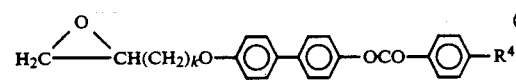
(XXXI)

The objective monomer (XXXI) may be prepared in the same manner as in the synthetic method (3) for preparing the compound wherein $R^3$ is

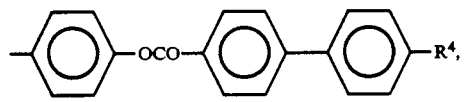

with the exception that hydroquinone is replaced by biphenyl-4,4'-diol, and the compound (XIV),

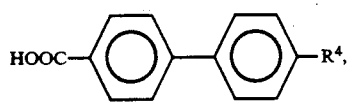

is replaced by the above-described compound (XXV),

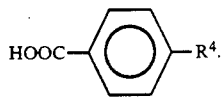

Other epoxy compounds containing aromatic rings A and/or B substituted with halogen atoms also may be synthesized according to the above-described methods.

Typical examples of the non-liquid-crystalline epoxy compound (c) represented by the general formula (5) having no helical structure, which is to be used as the other kind of copolymerizing monomer in the present invention, include ethylene oxide, propylene oxide, and 1,2-epoxyhexane.

The liquid-crystalline copolymer of the present invention is prepared by copolymerizing thus obtained two or more monomers having helical structures which are combined to include at least two epoxy compounds opposite in twining direction of helix to each other, or by copolymerizing thus obtained at least one liquid-crystalline monomer having a helical structure with at least one non-liquid-crystalline epoxy comonomer, and the copolymerization can be performed by using known cationic polymerization methods, or the like.

The catalysts that may be employed for the cationic copolymerization in the present invention are known ones including protonic acids, such as sulfuric acid, phosphoric acid or perchloric acid, lewis acids, such as boron trifluoride, aluminum chloride, titanium tetrachloride or stannic chloride, boron trifluoride etherate, etc. Among these catalysts, stannic chloride may be suitably used.

It is also possible to prepare the copolymers of the present invention by coordination polymerization by using organic aluminum complexes, etc. as a catalyst. In this case, copolymers having number average molecular weights of not less than 30,000 can be obtained.

The polymerization techniques that may be employed in the present invention are bulk polymerization technique, slurry polymerization technique, solution polymerization technique, etc., preferably solution polymerization technique.

The suitable polymerization temperature can be usually from 0° to 30° C., although it is not uniformly specified since it varies depending on the kind of the catalyst.

The suitable polymerization time can be usually from several hours to six days, although it varies depending on the other polymerization conditions including the polymerization temperature, etc.

The control of the molecular weights of the copolymers may be conducted by addition of a known molecular weight regulator and/or control of the concentration of catalyst to monomers.

When bulk polymerization technique is employed, the resulting copolymers may be directly fixed between a couple of substrates in a state adhering to the substrates by sufficiently mixing the monomers with an initiator, sufficiently de-aerating the mixture, introducing the mixture between two substrates such as glass substrates, and heating.

The solvents to be used in slurry polymerization and solution polymerization may be any known inert solvent. The illustrative examples of the solvents to be suitably used include hexane, dichloromethane or aromatic solvents, such as benzene, toluene, and xylene.

It is not essential but preferable to replace the atmosphere of the reaction system with an inert gas, such as argon or nitrogen, at the time of copolymerization reaction and the above-described epoxidation reaction.

Thus obtained copolymers of the present invention may be used by forming them into films by using a known film forming technique, such as casting technique, T-die technique, inflation technique, calender technique, stretching technique or the like. Thus obtained films of the copolymers of the present invention may be used in various optoelectronics fields, such as liquid crystal displays, electronic optical shutters, electronic optical diaphragms, and the like, by disposing them between a couple of large glass substrates, curved glass substrates, polyester films, etc., not to mention two usual glass substrates. Further, the polymers may also be directly formed into films adhering to a substrate by dissolving a copolymer in a suitable solvent, applying the resulting copolymer solution to a surface of a substrate, such as glass substrate, and then evaporating the solvent.

From the results of measurements of the helical pitch and phase transition temperature, it was confirmed that the copolymers of the present invention have extended helical pitches longer than the corresponding homopolymers and take chiral smectic C phase liquid crystal state over a wide temperature range including temperatures around room temperature. It was also confirmed that they perform high speed response at temperatures around room temperature.

The copolymers of the present invention have both the properties of smectic phase liquid crystal and the typical property of polymers, i.e., an excellent moldability, and they have a large possibility of usage in the fields of integrated optics, optoelectronics, and information memory. For instance, the copolymers of the present invention may be used as various electronic optical elements, for example, for liquid crystal displays, such as digital displays of various forms, electronic optical shutters, optical-path transfer switches in optical communication systems, electronic optical diaphragms, memory devices, optical modulators, liquid crystal optical printer heads, and varifocal lenses.

The copolymers of the present invention may be further improved by various treatments well known in this industry, for example, by mixing two or more copolymers of the present invention, mixing them with other polymers, addition of additives such as various inorganic or organic compounds or metals, including stabilizers, plasticizers, etc.

In order to fully and clearly illustrate the present invention, the following examples are presented. It is intended that the examples be considered illustrative rather than limiting the invention disclosed and claimed herein.

EXAMPLES 1 TO 18 AND COMPARATIVE EXAMPLES 1 TO 5

The structures of the polymers obtained in the Examples and Comparative Examples were identified by NMR, IR, and elementary analysis. The measurement of phase transition temperatures and identification of the phases were each conducted by the use of a DSC and a polarizing microscope, respectively.

Figure 2:
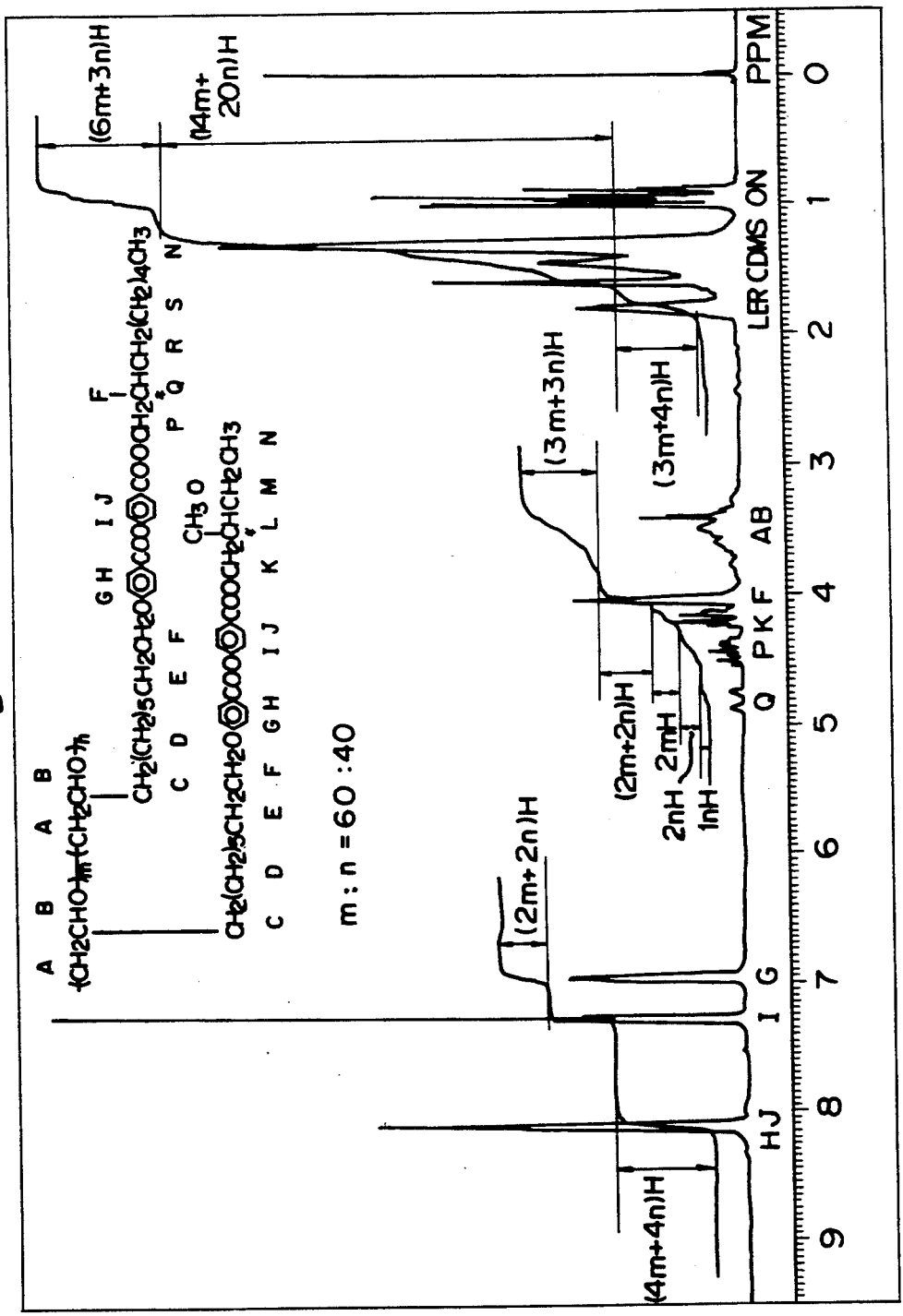
FIG. 2 is a chart showing an NMR spectrum of the liquid-crystalline copolymer prepared in Example 2.
Figure 3:
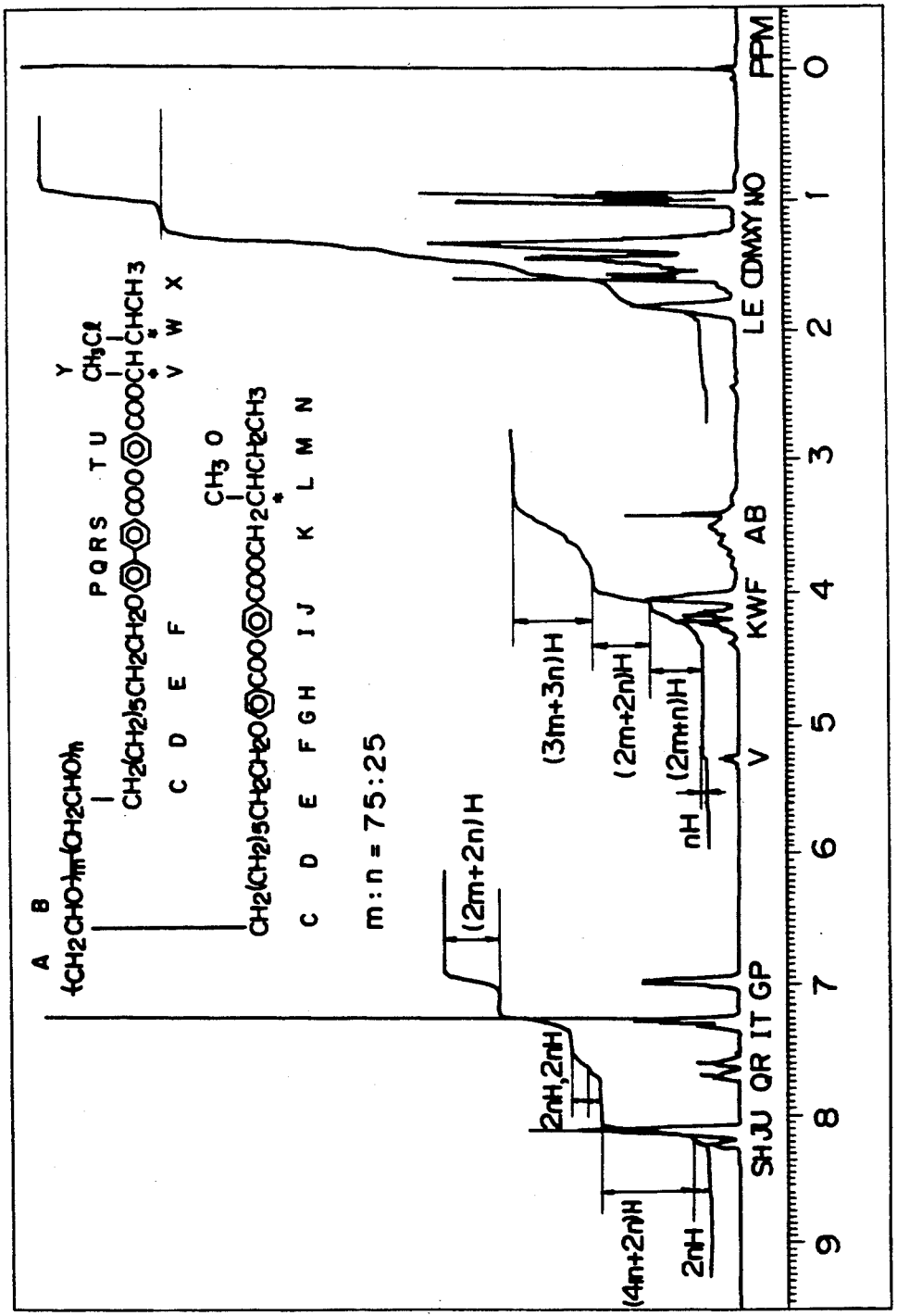
FIG. 3 is a chart showing an NMR spectrum of the liquid-crystalline copolymer prepared in Example 3.
Figure 4:
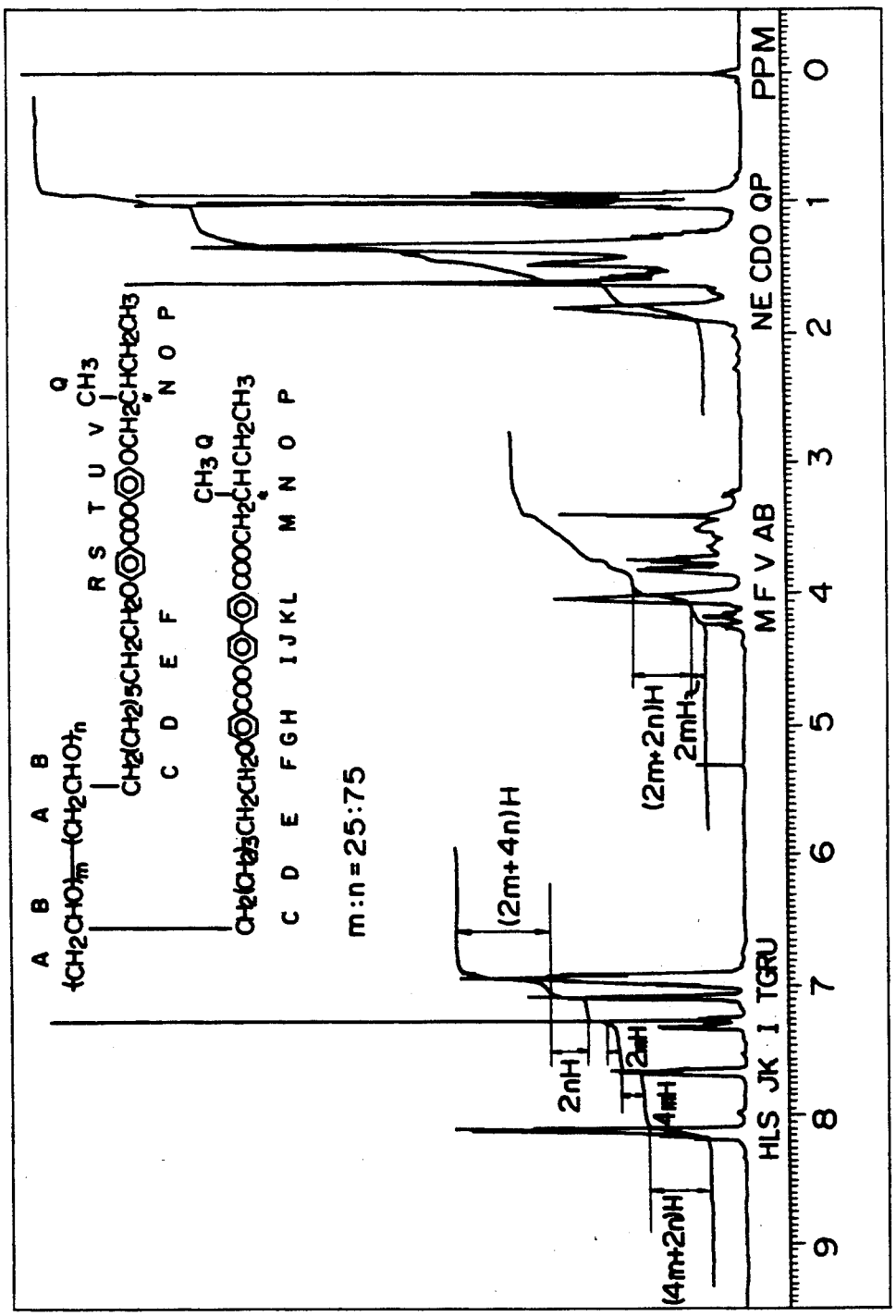
FIG. 4 is a chart showing an NMR spectrum of the liquid-crystalline copolymer prepared in Example 4.
Figure 5:
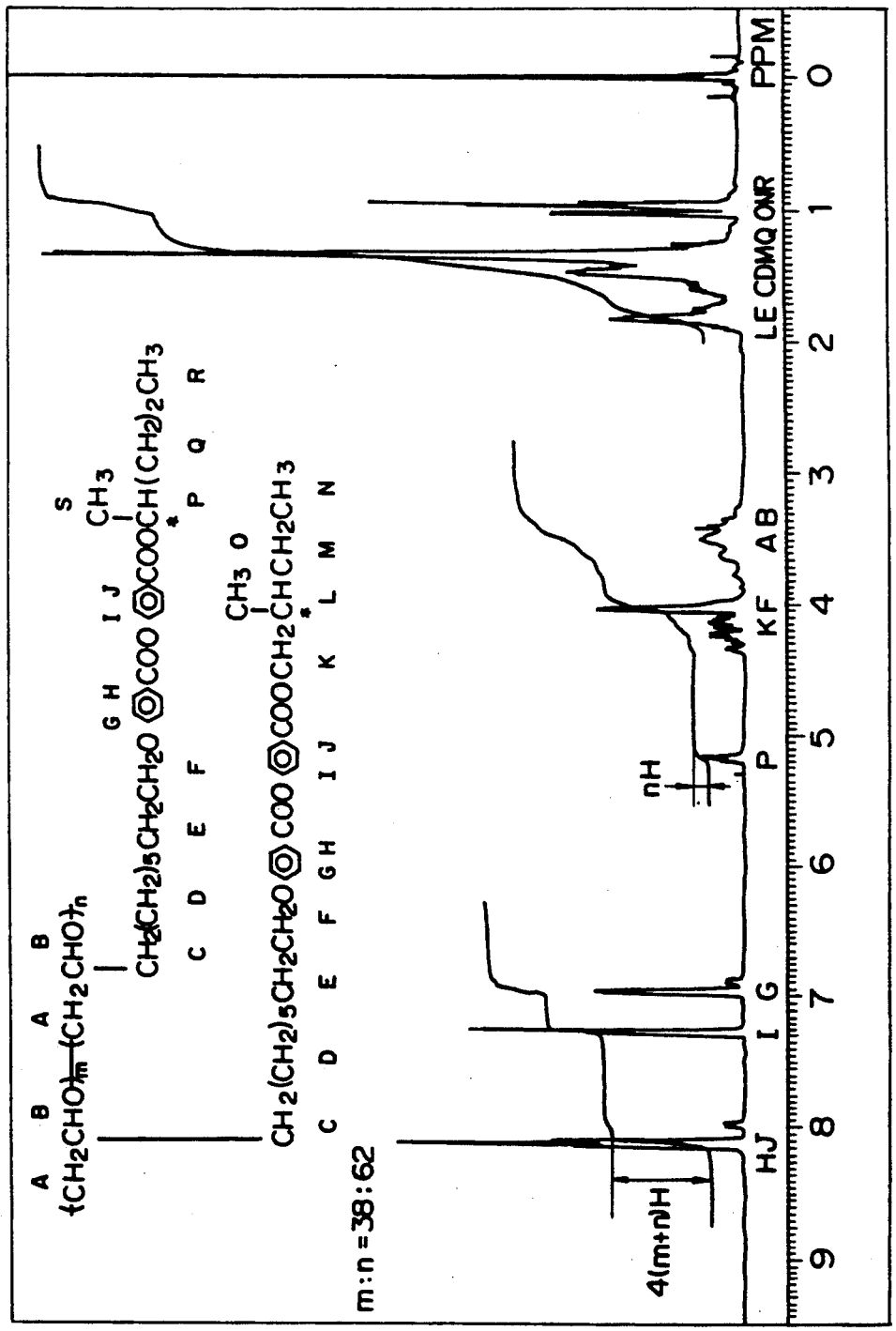
FIG. 5 is a chart showing an NMR spectrum of the liquid-crystalline copolymer prepared in Example 7.
Figure 6:
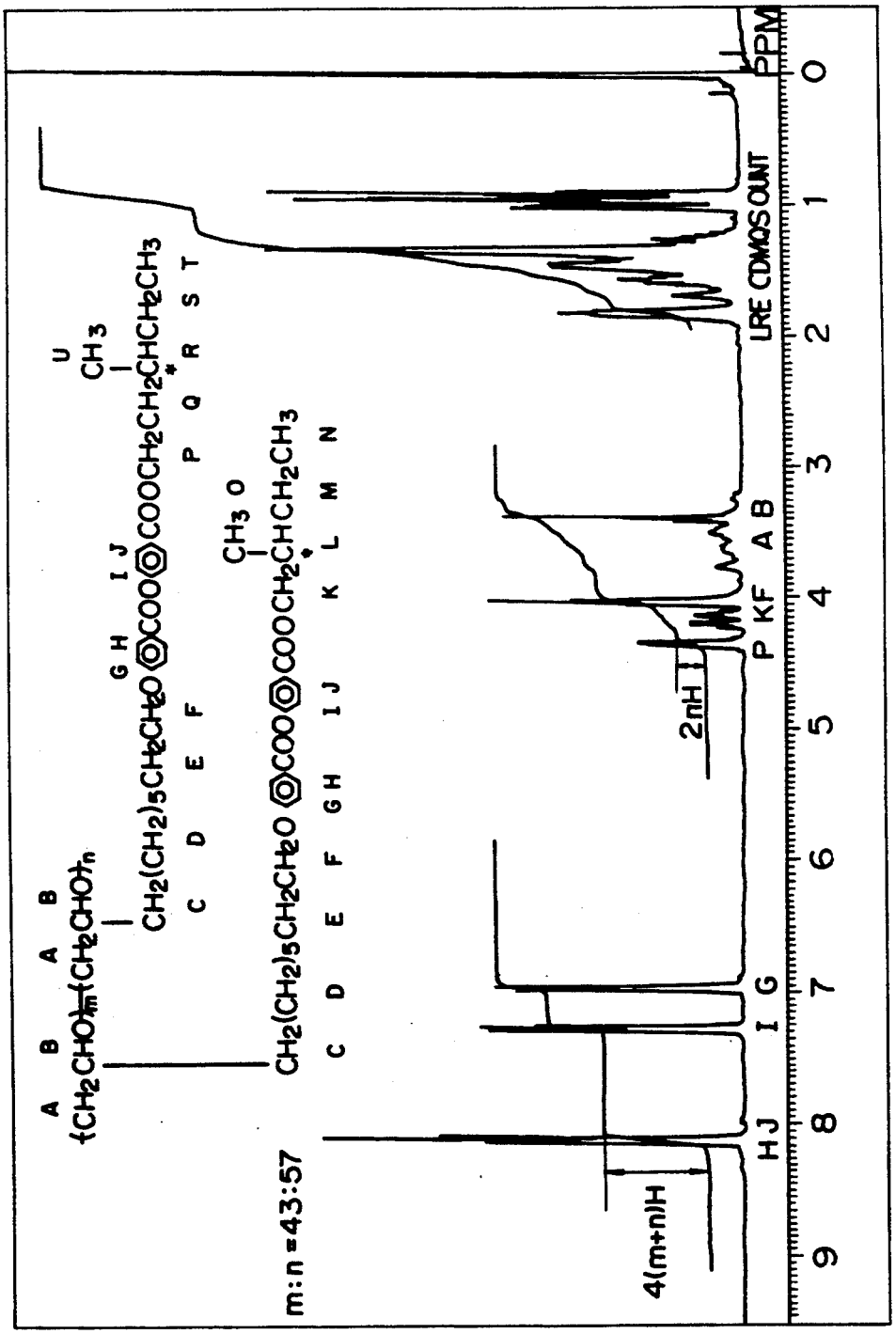
FIG. 6 is a chart showing an NMR spectrum of the liquid-crystalline copolymer prepared in Example 8.
Figure 7:
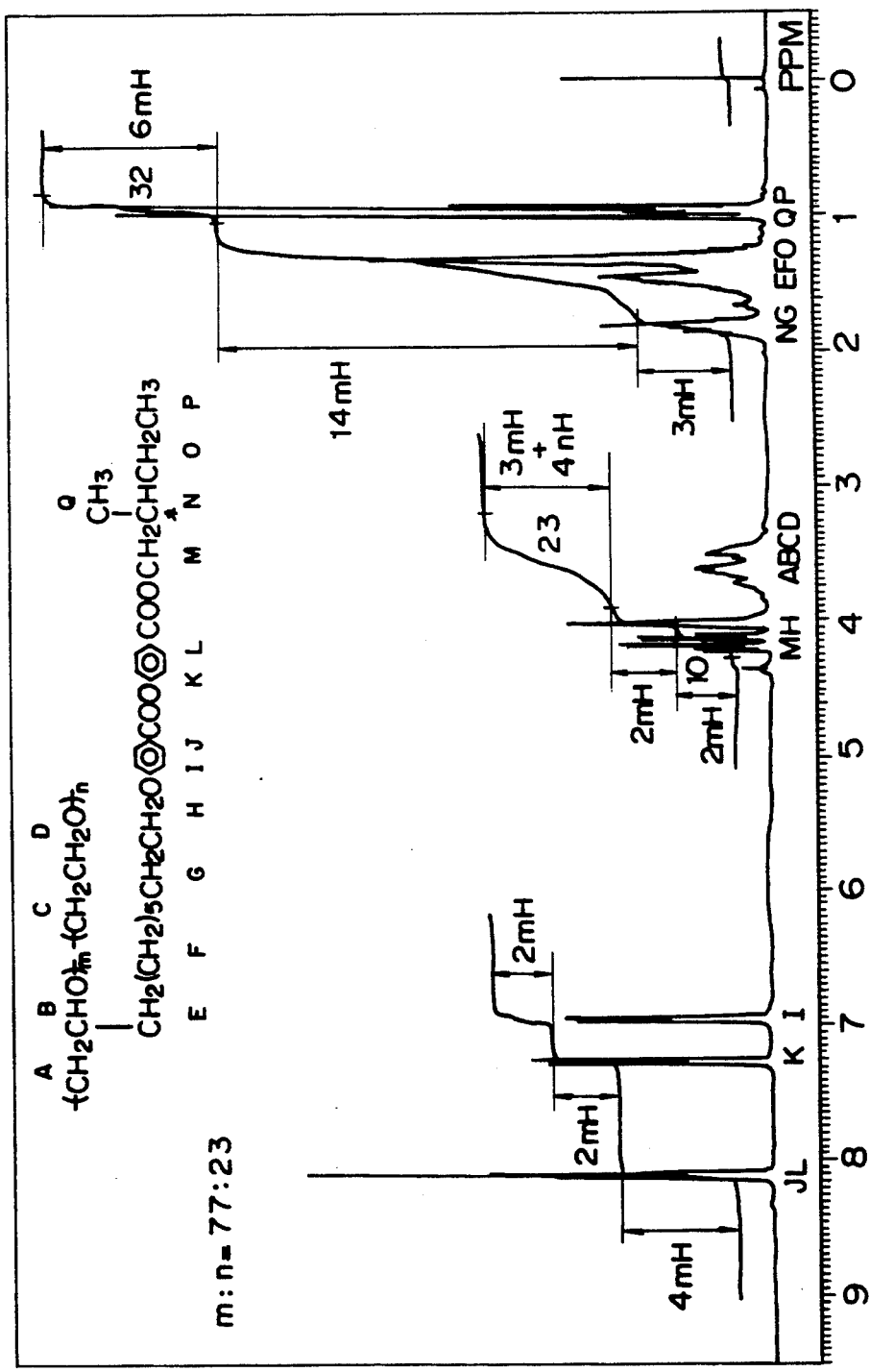
FIG. 7 is a chart showing an NMR spectrum of the liquid-crystalline copolymer prepared in Example 9.
Figure 8:
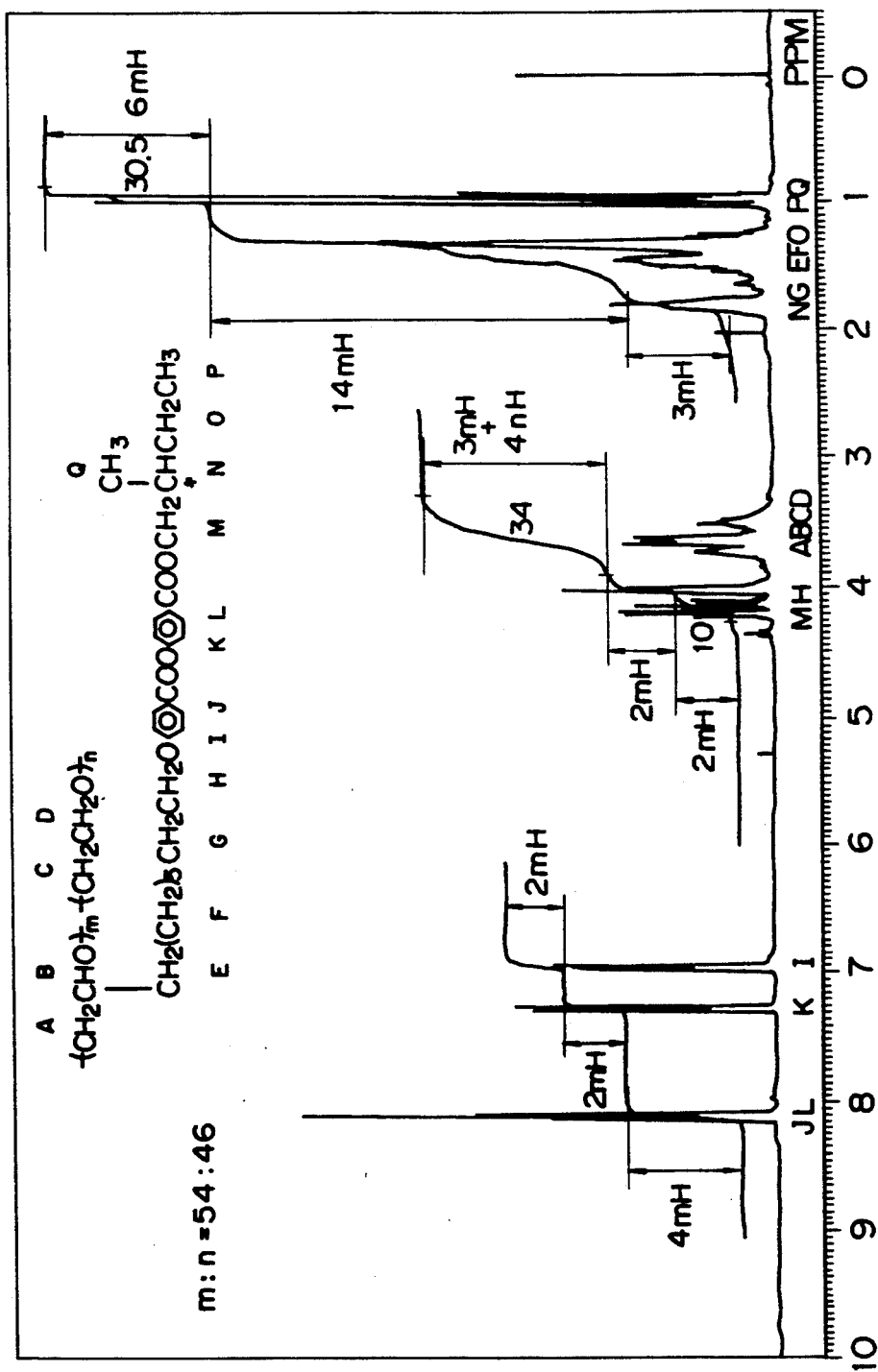
FIG. 8 is a chart showing an NMR spectrum of the liquid-crystalline copolymer prepared in Example 10.
Figure 9:
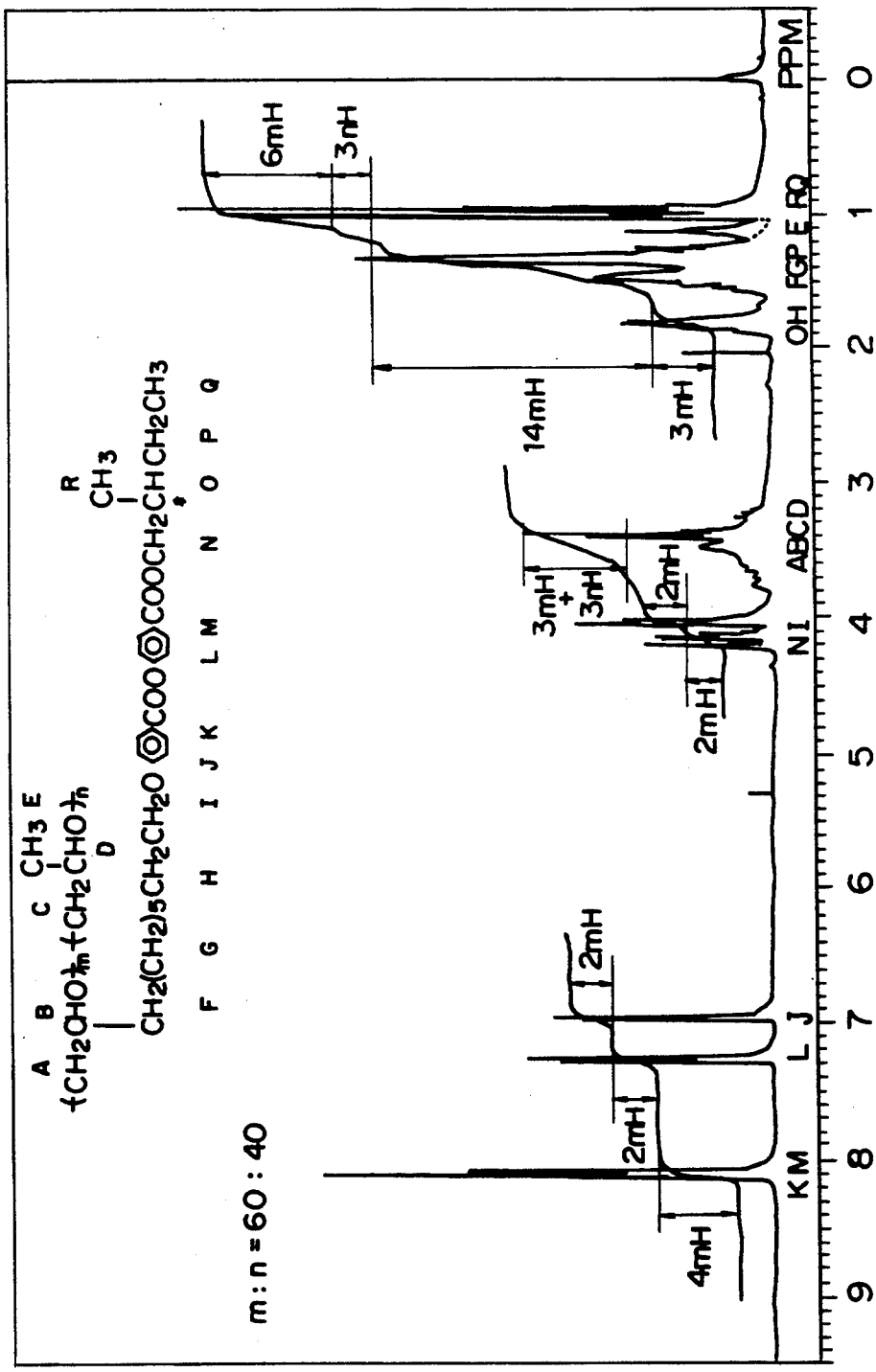
FIG. 9 is a chart showing an NMR spectrum of the liquid-crystalline copolymer prepared in Example 11.
Figure 10:
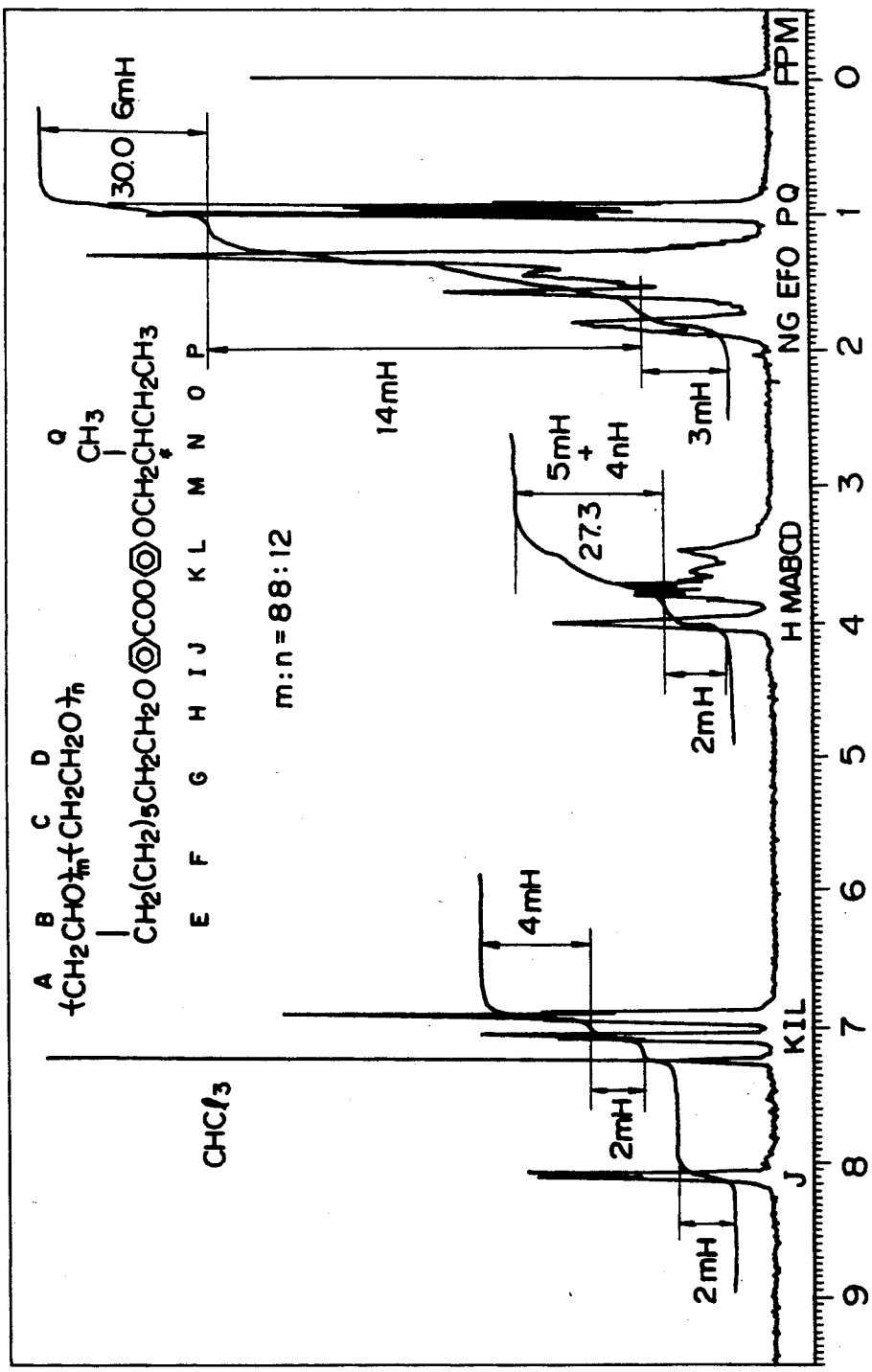
FIG. 10 is a chart showing an NMR spectrum of the liquid-crystalline copolymer prepared in Example 12.
Figure 11:
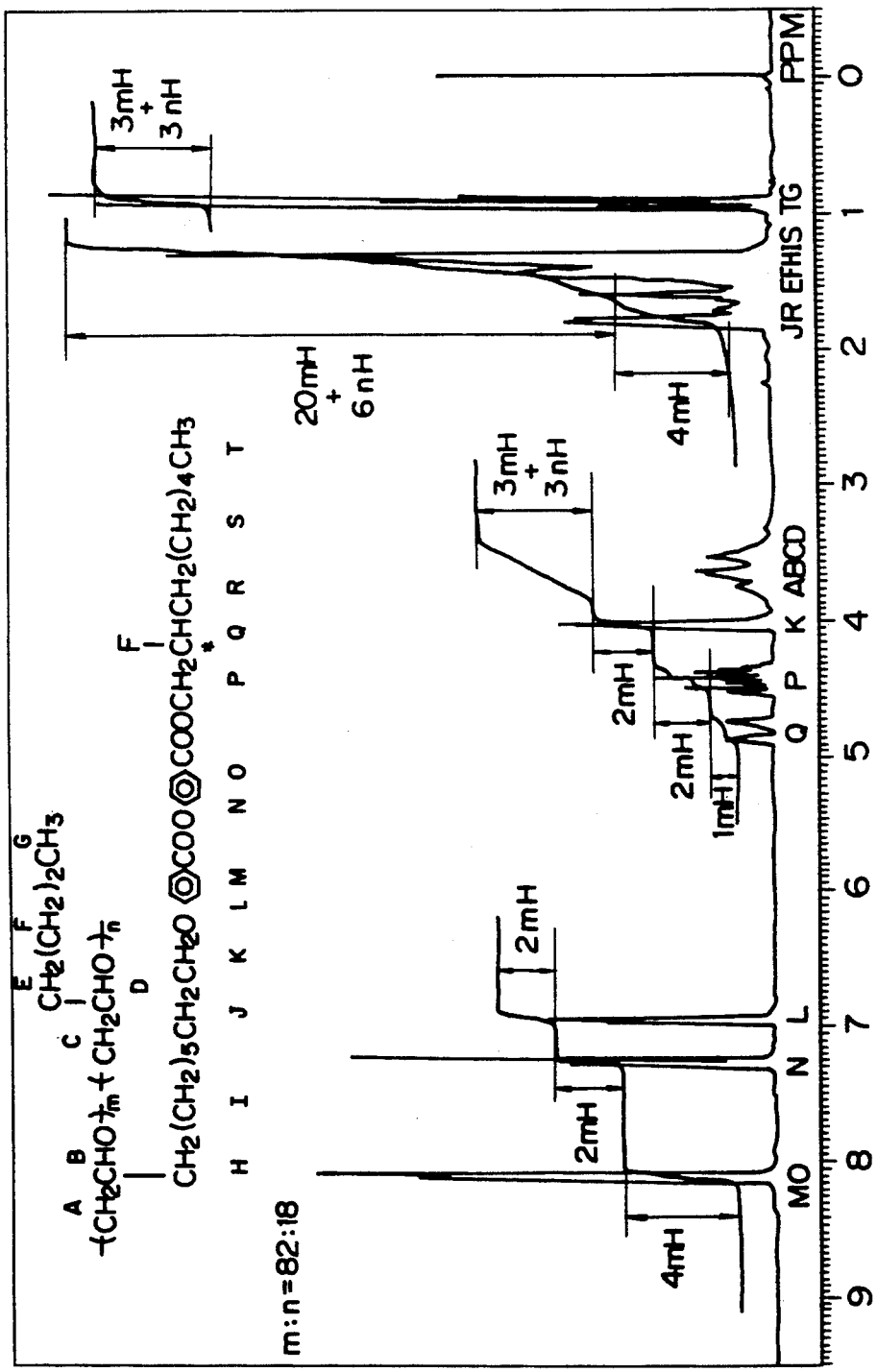
FIG. 11 is a chart showing an NMR spectrum of the liquid-crystalline copolymer prepared in Example 13.
Figure 12:
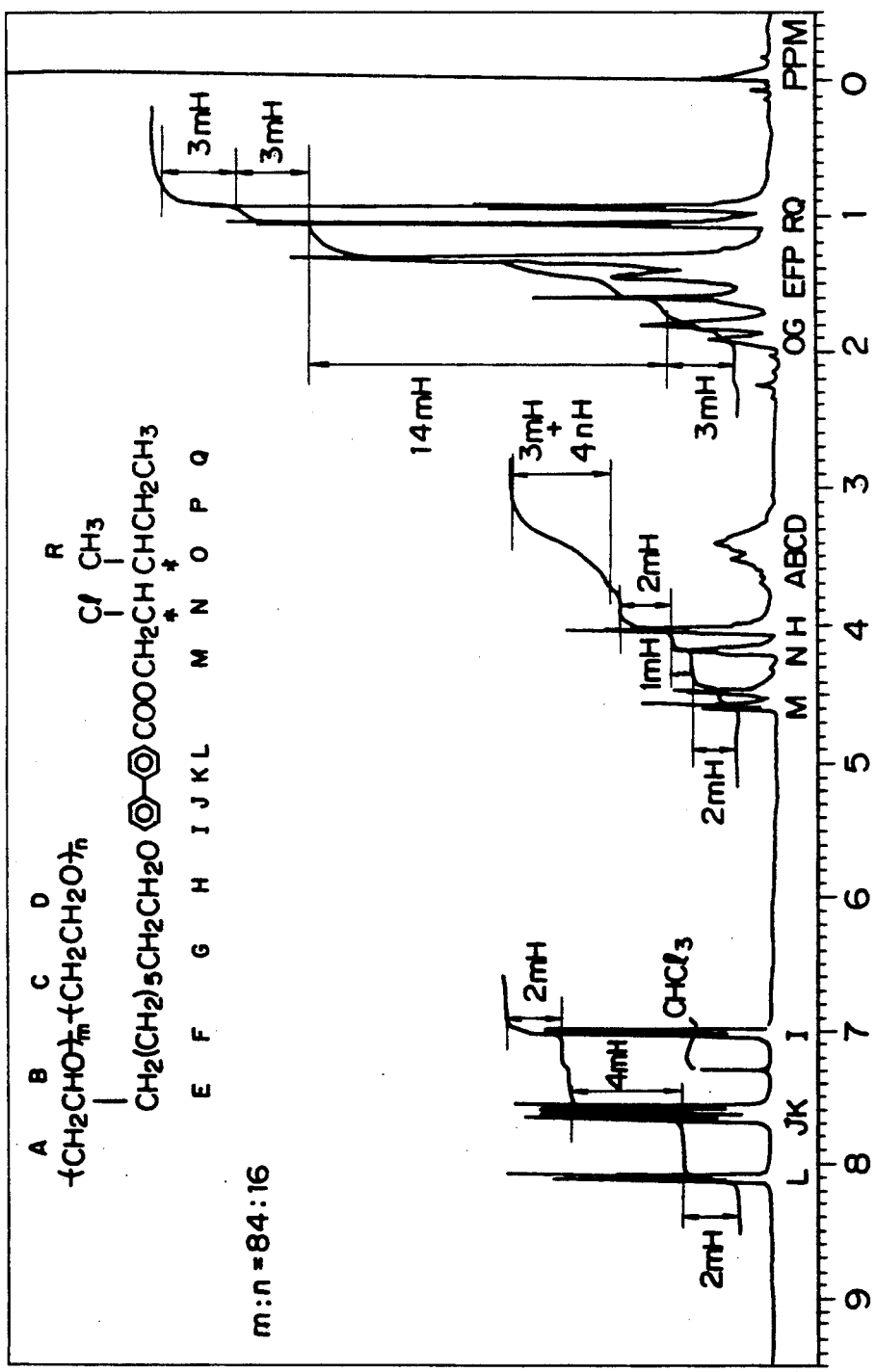
FIG. 12 is a chart showing an NMR spectrum of the liquid-crystalline copolymer prepared in Example 14.
Figure 13:
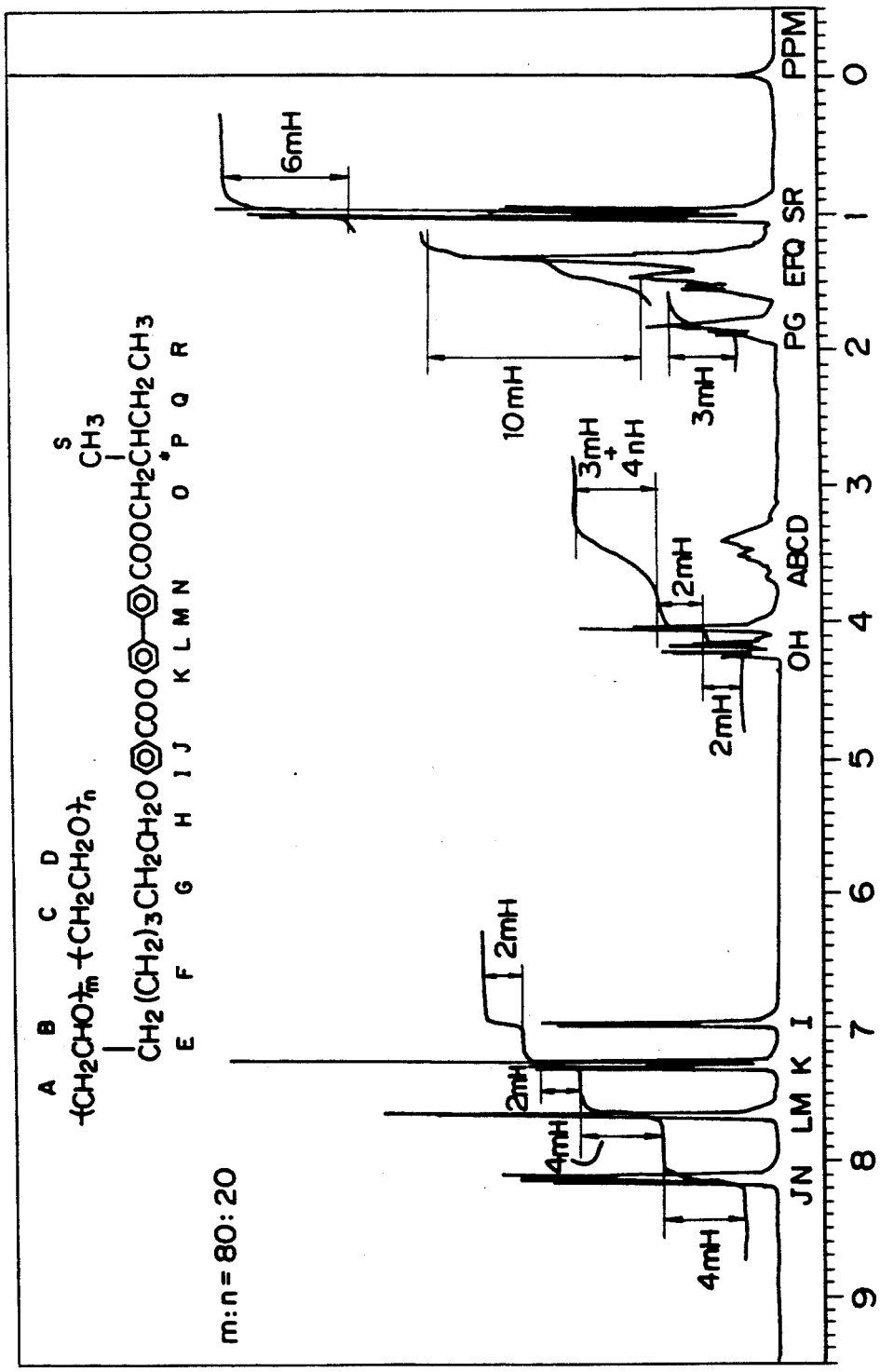
FIG. 13 is a chart showing an NMR spectrum of the liquid-crystalline copolymer prepared in Example 15.
Figure 14:
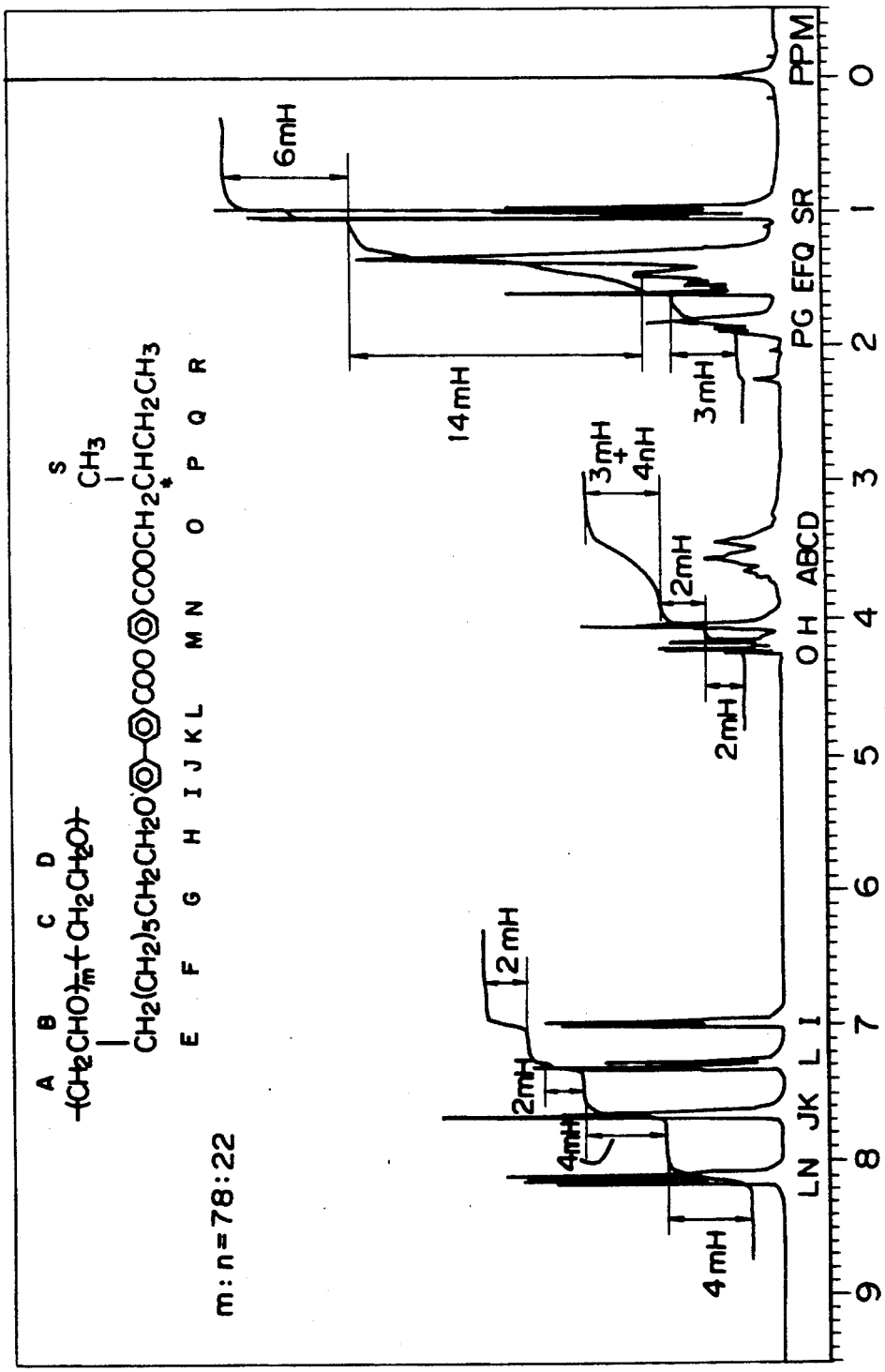
FIG. 14 is a chart showing an NMR spectrum of the liquid-crystalline copolymer prepared in Example 16.

The NMR charts of the copolymers obtained in Examples 1 to 4 are shown in FIGS. 1 to 4, respectively, and the NMR charts of the copolymers obtained in Examples 7 to 18 are shown in FIGS. 5 to 16, respectively.

The molar ratios of copolymer units, phase transition behaviors, helical pitches, and response speeds to electric field of the copolymers obtained in Examples 1 to 6 and the copolymers obtained in Examples 7 to 18 are shown in Tables 1 and 2, respectively. (g: glass state, Sm1: an unidentified smectic phase, SmC*: chiral smectic C phase, SmA: smectic A phase, N: nematic phase, N*: chiral nematic phase, Iso: isotropic phase.) The numerals in the phase transition behavior schemes represent the phase transition temperatures in °C unit.

The measurements of the twining direction, helical pitch, and response speed to electric field were conducted as follows.

Measurement of the Twining Direction

The twining direction of each liquid-crystalline epoxy compound having a helical structure was defined by placing, on a glass plate, the liquid-crystalline epoxy compound and a ferroelectric liquid crystal having a known twining direction next to each other, further placing a cover glass thereon, and then visually observing with a polarizing microscope whether the helical pitch in the mixed portion would become longer than those of the above two compounds (Contact method). A lengthened helical pitch indicates that these two compounds are opposite in twining direction of helix to each other.

Measurement of the Helical Pitch

A liquid crystal sample was supported between two untreated ITO substrates and was adjusted to 100 μm in thickness. Subsequently, the obtained specimen was heated up to the transition temperature to isotropic phase and was then cooled with a cooling speed of 1° C./min. During the drop in temperature, an optically microscopic photograph of the striped pattern appeared in SmC* phase was taken to calculate the helical pitch from the observed space between the stripes.

Measurement of the Response Speed to Electric Field

A polymer was supported between two ITO substrates of 20×10 mm and was adjusted to 25 μm in thickness by spacers. An alternative current of $E = 2 \times 10^6$ V/m was applied on the obtained specimen, and the response time required of the light transmittance to change from 0% to 90% was measured.

EXAMPLE 1

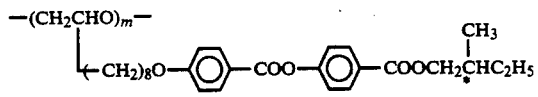

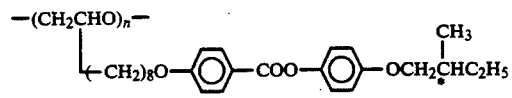

1.(1) Synthesis of 4-(2-methylbutoxy)phenol

Into a n-butanol suspension containing 37 mmol (9.0 g) of 2-methylbutyl p-toluenesulfonate prepared by tosylating S-(−)-2-methylbutanol and 74 mmol (8.2 g) of hydroquinone, added dropwise was a solution of 50 mmol (2.1 g) of sodium hydroxide dissolved in a solvent mixture comprising 3 ml of water and 10 ml of n-butanol, and the obtained mixture was then stirred for 8 hours at 120° C. After addition of water, the reaction solution was extracted with ether, and the extracted solution was dried and concentrated. The resulting concentrate was purified by column chromatography to obtain 4.8 g of the objective ether compound (Yield: 72%).

1.(2) Synthesis of 4-(2-methylbutoxy)phenyl 4-(9-decenyloxy)benzoate 10.0 g of 10-chloro-1-decene was allowed to react with 25 g of sodium iodide for 10 hours at 80° C. in 2-butanone to replace the chloro group with an iodo group. After the reaction solution was washed with water and dried, the solvent was removed out. To the resulting residue added were 11.5 g of ethyl p-hydroxybenzoate and 9.6 g of potassium carbonate, and the resulting mixture was then refluxed for 15 hours in absolute ethanol. Subsequently, to the reaction solution added was an aqueous solution of potassium hydroxide containing 4.0 g of potassium hydroxide, and the obtained mixture was heated for 5 hours at 80° C. After conclusion of the reaction, the reaction solution was acidified with hydrochloric acid and then concentrated under reduced pressure. Water was added to the residue to form a suspension, and the insoluble matter in the suspension was collected and dried, to obtain 9.5 of 4-(9-decenyloxy)benzoic acid. (Yield: 60%)

Subsequently, a toluene solution containing 10 mmol (2.8 g) of 4-(9-decenyloxy)benzoic acid and 30 mmol (3.6 g) of thionyl chloride was allowed to react for 3 hours at 100° C., and the resulting reaction solution was concentrated under reduced pressure to obtain an acid chloride compound. A solution of the acid chloride compound dissolved in 5 ml of THF was added dropwise in a solution of 8 mmol (1.4 g) of the ether compound obtained in 1.(1) and 2 ml of triethylamine dissolved in 20 ml of THF, and the obtained mixture was stirred for 10 hours. After addition of water, the reaction solution was extracted with ether, and the extracted solution was dried and concentrated. The concentrate was then purified by column chromatography to obtain 2.2 g of the objective alkene compound.

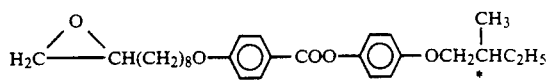

1.(4) Synthesis of 2-methylbutyl p-hydroxybenzoate 4.0 g of p-hydroxybenzoic acid and 12.5 g of (S)-(−)-2-methylbutanol were refluxed for 6 hours in toluene in the presence of sulfuric acid, while the generated water was removed out. Subsequently, the reaction solution was washed with water to remove sulfuric acid out. After the resulting solution was dried and concentrated, the concentrate was purified by column chromatography to obtain 5.0 g of the objective ester compound (liquid state at room temperature, $[\alpha]_D^{23} = +4.9°$ (CHCl$_3$)). (Yield: 83%)

1.(5) Synthesis of 2-methylbutyl 4-[4'-(9-decenyloxy)benzoloxy]benzoate

To 4.5 g of 4-(9-decenyloxy)benzoic acid prepared in the same manner as in 1.(2) added was toluene, and the mixture was cooled in an ice bath. During cooling of the mixture in the ice bath, 3.5 g of thionyl chloride was further added dropwise to the mixture. After conclusion of dropping, reaction was carried out for 7 hours at 80° C. After conclusion of the reaction, the reaction solution was concentrated to obtain an acid chloride compound. While, 4.5 g of 2-methylbutyl 4-hydroxybenzoate obtained in 1.(4) and 1.8 g of pyridine were dissolved in toluene and the obtained solution was cooled in an ice bath. Thereto added dropwise was a toluene solution of the above-described acid chloride compound. After conclusion of dropping, reaction was carried out for 5 hours at 50° C. After conclusion of the reaction, the product was washed with water and dried over magnesium sulfate, to obtain 5.5 g of the objective alkene compound. (Yield: 72%)

1.(6) Epoxidation 5.5 g of the alkene compound obtained in 1.(5) was subjected to the same procedure as in 1.(3), to obtain 5.2 g of a monomer (R configuration) represented by the following formula. (Yield: 92%)

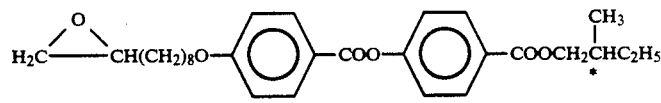

(Yield: 63%)

1.(3) Epoxidation

After a stream of gaseous argon was passed through a solution of 2 mmol (0.84 g) of the alkene compound obtained in 1.(2) and 3 mmol (0.52 g) of m-chloroperbenzoic acid dissolved in 10 ml of methylene chloride to displace the air in the solution and the reaction apparatus, the solution was stirred for 10 hours. The resulting reaction solution was washed with an aqueous potassium carbonate solution, dried, and concentrated, to obtain 0.82 g of a monomer (L configuration) represented by the following formula. (Yield: 90%)

1.(7) Synthesis of Polymer

After a stream of gaseous argon was passed through a solution of 1.0 mmol (0.48 g) of the monomer synthesized in 1.(6) and 1.0 mmol (0.45 g) of the monomer synthesized in 1.(3) dissolved in 10 ml of methylene chloride to displace the air in the solution and the reaction apparatus, 0.20 mmol of stannic chloride was added to the solution, and the mixture was allowed to stand for 5 days at room temperature. After the resulting reaction solution was concentrated, the concentrate was purified by column chromatography to obtain 0.70 g of a polymer (conversion rate: 75%, Mn=3,200, copolymerization ratio m:n according to NMR spectrum=58:42).

EXAMPLE 2

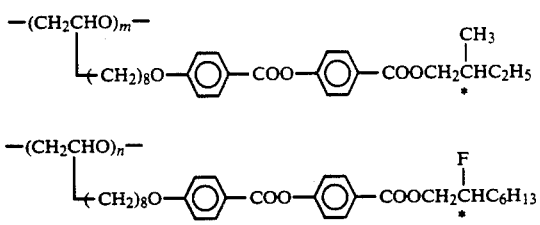

2.(1) Synthesis of 2-fluorooctyl p-hydroxybenzoic acid 11 g of thionyl chloride was added dropwise to 5.4 g of p-acetoxybenzoic acid. The mixture was then heated to 80° C. and wan allowed to react for 3 hours. After conclusion of the reaction, the excessive thionyl chloride was distilled out from the reaction solution under reduced pressure to obtain an acid chloride compound. The acid chloride compound was dissolved in toluene and the obtained solution was then cooled in an ice bath. Thereto added was a toluene solution containing 4.4 g of (−)-2-fluorooctanol and 3 g of pyridine. The resulting mixture was stirred overnight at room temperature. After conclusion of the reaction, the reaction solution was washed with water, dried, and concentrated under reduced pressure. The resulting residue was dissolved in ether. 10 g of benzyl amine was added dropwise to the solution. The mixture was stirred for 5 hours at room temperature. After conclusion of the reaction, the product was washed with water, dried and concentrated under reduced pressure. The resulting residue was purified by column chromatography to obtain 4.9 g of the objective ester compound. (Yield: 73%)

2.(2) Synthesis of 2-fluorooctyl 4-[4′-(9-decynyloxy)benzoyloxy]benzoate

To 3.0 g of 4-(9-decenyloxy)benzoic acid prepared in the same manner as in 1.(2) in Example 1 added was toluene, and the mixture was cooled in an ice bath. 2.0 g of thionyl chloride was added to the toluene solution dropwise. Subsequently, reaction was carried out at 80° C. for 3 hours. After conclusion of the reaction, the product was concentrated to obtain an acid chloride compound. While, 1.7 g of 2-fluorooctyl 4-hydroxybenzoate obtained in 2.(1) and 0.9 g of pyridine were dissolved in toluene, and the resulting solution was cooled in an ice bath. Thereto added dropwise was a toluene solution of the above-described acid chloride compound. Subsequently, reaction was carried out at room temperature for 15 hours. After conclusion of the reaction, the product was washed with water and dried over magnesium sulfate, and the the solvent was removed out from the dried product under reduced pressure. The residue was purified by column chromatography to obtain 2.8 g of the objective ester compound. (Yield: 85%)

2.(3) Epoxidation 2.8 g of the ester compound obtained in 2.(2) was subjected to the same procedure as in 1.(3) in Example 1, to obtain 2.6 g of a monomer (L configuration) represented by the following formula. (Yield: 91%)

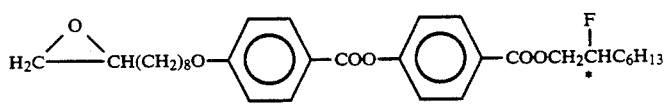

2.(4) Synthesis of Polymer

After a stream of gaseous argon was passed through a solution of 1.0 mmol (0.48 g) of the monomer synthesized in 1.(6) in Example 1 and 1.0 mmol (0.54 g) of the monomer synthesized in 2.(3) dissolved in 10 ml of methylene chloride to displace the air in the solution and the reaction apparatus, 0.20 mmol of stannic chloride was added to the solution, and the mixture was then allowed to stand for 5 days at room temperature. After concentration of the reaction solution, the concentrate was purified by column chromatography to obtain 0.72 g of a polymer (conversion rate: 71%, Mn=2,500, co-polymerization ratio m:n according to NMR spectrum=60:40).

EXAMPLE 3

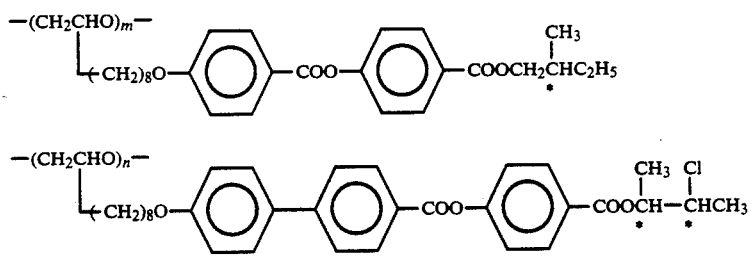

3.(1) Synthesis of 2-chloro-1-methylpentyl 4-hydroxybenzoate

A solution of 30 mmol (5.4 g) of 4-acetoxybenzoic acid and 90 mmol (10.8 g) of thionyl chloride dissolved in 100 ml of toluene was stirred for 2 hours at 80° C., and the reaction solution was concentrated under reduced pressure, to obtain an acid chloride compound. Into a solution of 10 mmol (1.1 g) of (−)-3-chloro-2-butanol and 5 ml of triethylamine dissolved in 30 ml of THF added dropwise was a solution of the above acid chloride compound dissolved in 10 ml of THF, and the mixture was then stirred for 10 hours. After concentration of the reaction solution, water was added to the concentrate, and the resulting mixture was then extracted with ether. After concentration of the extracted solution, the concentrate was dissolved in 200 ml of ether, and the resulting solution was stirred for 5 hours after addition of 20 ml of benzylamine. The reaction solution was washed with water and then purified by column chromatography to obtain 1.6 g of the objective hydroxy compound. (Yield: 70%)

3.(2) Synthesis of 2-chloro-1-methylpentyl 4-[4'-{4''-9-decenyloxy)phenyl}benzoyloxy]benzoate A solution of 7 mmol (2.5 g) of 4-[4'-(9-decenyloxy)-phenyl]benzoic acid and 21 mmol (2.5 g) of thionyl chloride dissolved in 30 ml of toluene was stirred for 2 hours at 80° C., and the resulting reaction solution was concentrated under reduced pressure to obtain an acid chloride compound. A solution of the acid chloride compound dissolved in 5 ml of THF ws added dropwise into a solution of 5 mmol (1.1 g) of the hydroxy compound obtained in 3.(1) and 2 ml of triethylamine dissolved in 20 ml of THF, and the mixture was stirred for 10 hours. After concentration of the reaction solution, water was added to the concentrate, and the mixture was extracted with ether. After concentration of the extracted solution, the concentrate was purified by column chromatography to obtain 2.2 g of the objective alkene compound. (Yield: 78%)

3.(3) Epoxidation

After a stream of gaseous argon was passed through a solution of 2 mmol (1.13 g) of the alkene compound obtained in 3.(2) and 3 mmol (0.52 g) of m-chloropebenzoic acid dissolved in 10 ml of methylene chloride to displace the air in the solution and the reaction apparatus, the solution was stirred for 10 hours. The reaction solution was washed with an aqueous potassium carbonate solution, dried, and concentrated, to obtain 1.11 g of a monomer (L configuration) represented by the following formula. (Yield: 96%)

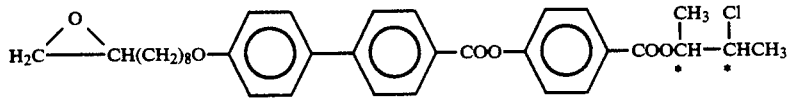

3.(4) Synthesis of Polymer

After a stream of gaseous argon was passed through a solution of 1.6 mmol (0.77 g) of the monomer synthesized in 1.(6) in Example 1 and 1.0 mmol (0.23 g) of the monomer obtained in 3.(3) dissolved in 10 ml of methylene chloride to displace the air in the solution and the reaction apparatus, 0.04 mmol of stannic chloride was added to the solution, and the mixture was allowed to stand for 5 days at room temperature. After concentration of the reaction solution, the concentrate was purified by column chromatography to obtain 0.81 g of a polymer (conversion rate: 81%, Mn=2,800, copolymerization ratio m:n according to NMR spectrum=75:25).

EXAMPLE 4

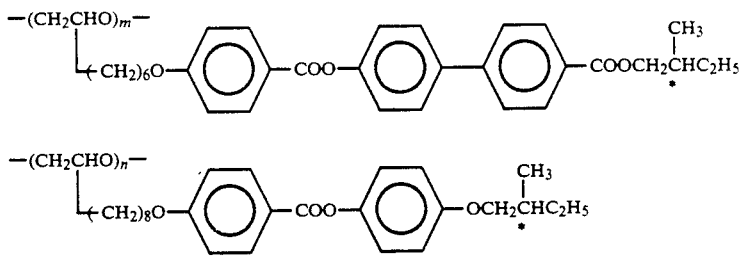

4.(1) Synthesis of p-(7-octenyloxy)benzoic acid 9.4 g of 8-bromo-1-octene, 9.0 g of ethyl p-hydroxybenzoate, and 7.6 g of potassium carbonate were refluxed in ethanol for 10 hours. Thereto added was an aqueous solution containing 2.4 g of sodium hydroxide, and then reflux was further continued for 10 hours. After conclusion of the reaction, the reaction solution was diluted with water, and the pH of the solution was lowered to 2 by dropping hydrochloric acid. The generated precipitate was collected, washed sufficiently with water, and dried, to obtain 10.8 g of the objective ether compound. (Yield: 89%)

4.(2) Synthesis of 2-methylbutyl 4-[p-(7-octenyloxy)benzoyloxy]biphenyl-4-carboxylate 9 g of p-(7-octenyloxy)benzoic acid obtained in 4.(1) was suspended in toluene, and the suspension was cooled in an ice bath. Thereto added dropwise was 6 g of thionyl chloride. After conclusion of dropping, the temperature was raised, and reaction was carried out for 6 hours at 80° C. After conclusion of the reaction, the reaction solution was concentrated under reduced pressure to obtain an acid chloride compound. Toluene was added to the acid chloride compound to form a toluene solution, and the toluene solution was cooled in an ice bath.

A toluene solution containing 10 g of 2-methylbutyl 4'-hydroxybiphenyl-4-carboxylate and 3 g of pyridine was added dropwise to the above-described toluene solution of the acid chloride compound. After conclusion of dropping, the temperature was raised, and reaction was carried out for 8 hours at 50° C. After conclusion of the reaction, the product was washed with water and dried over magnesium sulfate, and the dried product was concentrated under reduced pressure. The residue was recrystallized from ethanol to obtain 8.2 g of the objective ester compound. (Yield: 45%)

4.(3) Epoxidation 7.2 g of the ester compound obtained in 4.(2) was oxidized with 3 g of m-chloroperbenzoic acid, to obtain 6.3 g of a monomer (R configuration) represented by the following formula. (Yield: 85%)

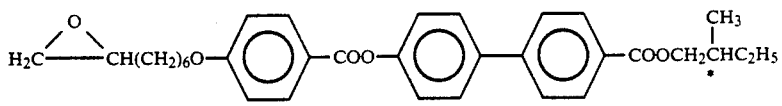

4.(4) Synthesis of Polymer

After a stream of gaseous argon was passed through a solution of 1.6 mmol (0.72 g) of the monomer synthesized in 1.(3) in Example 1 and 0.4 mmol (0.21 g) of the monomer synthesized in 4.(3) dissolved in 10 ml of methylene chloride to displace the air in the solution and reaction apparatus, 0.20 mmol of stannic chloride was added to the solution, and the mixture was allowed to stand for 5 days at room temperature. After concentration of the reaction solution, the concentrate was purified by column chromatography, to obtain 0.55 g of a polymer (conversion rate: 59%, Mn=2,400, copolymerization ratio m:n according to NMR spectrum=25:75)

EXAMPLE 5

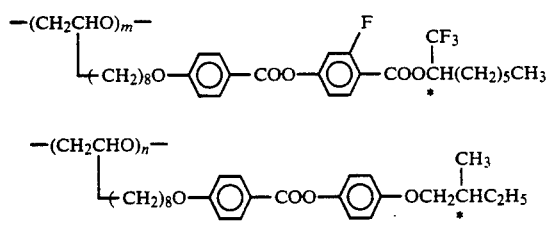

5.(1) Synthesis of 1-trifluoromethylheptyl 4-hydroxy-2-fluorobenzoate

The procedure as in 2.(1) in Example 2 was repeated with the exception that 20 mmol of 4-acetoxy-2-fluorobenzoic acid and 15 mmol of R-(+)-1,1,1-trifluoro-2-octanol were used as the raw materials, to obtain the objective hydroxy compound.

5.(2) Synthesis of 1-trifluoromethylheptyl 4-[4'-(9-decenyloxy)benzoyloxy]-2-fluorobenzoate The procedure as in 3.(2) in Example 3 was repeated with the exception that 5 mmol of the carboxylic acid synthesized in 1.(2) in Example 1 and 3 mmol of the hydroxy compound obtained in 5.(1) were used as the raw materials, to synthesize the objective alkene compound. (Yield: 69%)

5.(3) Epoxidation

The procedure as in 2.(3) in Example 2 was repeated with the exception that 2.0 mmol (1.16 g) of the alkene compound obtained in 5.(2) was used as the raw material, to synthesize a monomer (R configuration) represented by the following formula. (Yield: 86%)

5.(4) Synthesis of Polymer

The procedure as in 1.(4) in Example 1 was repeated with the exception that 1.0 mmol (600 mg) of the monomer obtained in 5.(3) and 1.0 mmol (450 mg) of the monomer obtained in 1.(3) in Example 1 were used as the raw materials, to synthesize a polymer (conversion rate: 68%, Mn=2,500, copolymerization ratio m:n according to NMR spectrum=48:52).

EXAMPLE 6

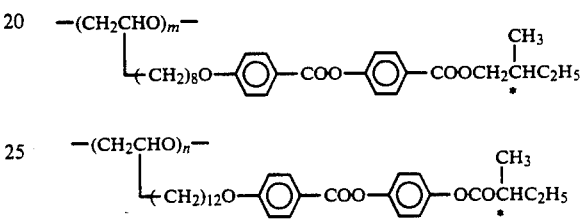

6.(1) Synthesis of 4-(2-methylbutanoyloxy)phenol

Into a solution of 50 mmol (5.1 g) of S-(+)-2-metylbutanoic acid and 100 mmol (11.0 g) of hydroquinone dissolved in 150 ml of toluene added was 1 ml of concentrated sulfuric acid, and the mixture was refluxed for 3 hours with stirring. After concentration of the reaction solution, the concentrate was purified by column chromatography to obtain 7.1 g of the objective hydroxy compound. (Yield: 73%)

6.(2) Synthesis of 4-(2-methylbutanoyloxy)phenyl 4-(13-tetradecenyloxy)benzoate The procedure as in 3.(2) in Example 3 was repeated with the exception that 15 mmol (5.0 g) of 4-(13-tetradecenyloxy)benzoic acid and 10 mmol (1.9 g) of the hydroxy compound obtained in 6.(1) were used as the raw materials, to obtain the objective alkene compound (Yield: 80%)

6.(3) Epoxidation

The procedure as in 1.(3) in Example 1 was repeated with the exception that 2.0 mmol (1.0 g) of the alkene compound obtained in 6.(2) was used as the raw material, to synthesize a monomer (L configuration) represented by the following formula. (Yield: 93%)

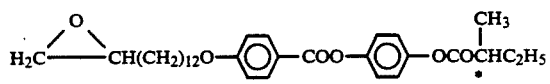

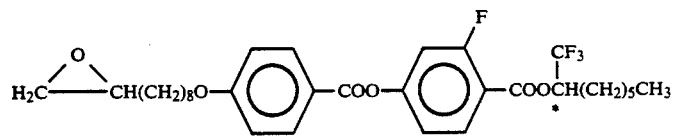

6.(4) Synthesis of Polymer

The procedure as in 1.(4) in Example 1 was repeated with the exception that 1.0 mmol (510 mg) of the monomer obtained in 6.(3) and 1.0 mmol (480 mg) of the monomer synthesized in 1.(6) in Example 1 were used as the raw materials, to synthesize a polymer (conversion rate: 82%, Mn=2,500, copolymerization ratio m:n according to NMR spectrum=55:45).

COMPARATIVE EXAMPLE 1

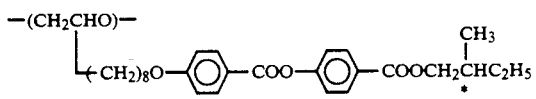

(1) Synthesis of Polymer

The polymer having the repeating unit represented by the above formula was synthesized by using the monomer synthesized in 1.(6) in Example 1, in the same manner as in Example 1. (conversion rate: 83%, Mn=2,100)

COMPARATIVE EXAMPLE 2

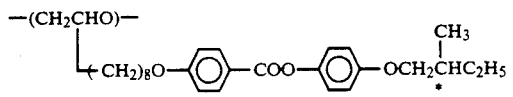

(1) Synthesis of Polymer

The polymer having the repeating unit represented by the above formula was synthesized by using the monomer synthesized in 1.(3) in Example 1, in the same manner as in Example 1. (conversion rate: 77%, Mn=2,500)

EXAMPLE 7

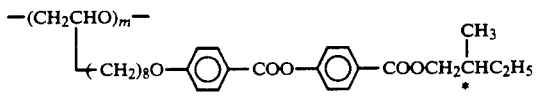

7.(1) Synthesis of 1-methylbutyl p-hydroxybenzoate

To 9.0 g of p-acetoxybenzoic acid added dropwise was 12 g of thionyl chloride. The mixture was heated to 80° C., and was then allowed to react for 3 hours. After conclusion of the reaction, the excessive thionyl chloride was distilled out from the reaction solution under reduced pressure, to obtain an acid chloride compound. The acid chloride compound was dissolved in toluene, and the obtained toluene solution was cooled in an ice bath. Into the toluene solution added dropwise dropwise was a toluene solution containing 3.5 g of S-(+)-2-pentanol and 0.5 g of pyridine. The resulting mixture was stirred overnight at room temperature. After conclusion of the reaction, the reaction solution was washed with water, dried, and concentrated under reduced pressure. The residue was dissolved in ether. Into the ether solution added dropwise was 10 g of benzylamine. The mixture was stirred for 5 hours at room temperature. After conclusion of the reaction, the product was washed with water, dried, and concentrated under reduced pressure. The residue was purified by column chromatography, to obtain 5.9 g of the objective ester compound. (Yield: 71%)

7.(2) Synthesis of 1-methylbutyl 4-[4'-(9-decenyloxy)benzoyloxy]benzoate

To 5.5 g of 4-(9-decenyloxy)benzoic acid obtained in the same manner as in 1.(2) in Example 1 added was toluene, and the mixture was cooled in an ice bath. 7.4 g of thionyl chloride was added dropwise to the mixture. Subsequently, reaction was carried out for 3 hours at 80° C. After conclusion of the reaction, the product was concentrated to obtain an acid chloride compound. While, 3.1 g of 1-methylbutyl 4-hydroxybenzoate obtained in 7.(1) and 0.9 g of pyridine were dissolved in toluene, and the toluene solution was cooled in an ice bath. Added dropwise thereto was a toluene solution of the above-described acid chloride compound. Subsequently, reaction was carried out for 6 hours at room temperature. After conclusion of the reaction, the product was washed with water and dried over magnesium sulfate, and the solvent was then distilled out from the dried product under reduced pressure. The residue was purified by column chromatography, to obtain 6.5 g of the objective ester compound. (Yield: 94%)

7.(3) Epoxidation 2.5 g of the ester compound obtained in 7.(2) was subjected to the same procedure as that in 1.(3) in Example 1, to obtain 2.2 g of a monomer (L configuration) represented by the following formula. (Yield: 85%)

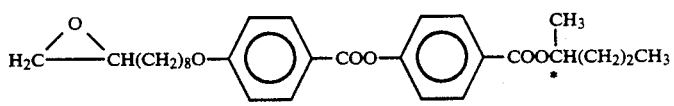

7.(4) Synthesis of Polymer

After a stream of gaseous argon was passed through a solution of 0.8 mmol (0.39 g) of the monomer synthesized in 1.(6) in Example 1 and 1.2 mmol (0.60 g) of the monomer synthesized in 7.(3) dissolved in 10 ml of methylene chloride to displace the air in the solution and reaction apparatus, 0.20 mmol of stannic chloride was added to the solution, and the mixture was allowed to stand for 5 days at room temperature. After concentration of the reaction solution, the concentrate was purified by column chromatography, to obtain 0.73 g of a polymer (conversion rate: 74%, Mn=2,800, copolymerization ratio m:n according to NMR spectrum=38:62).

EXAMPLE 8

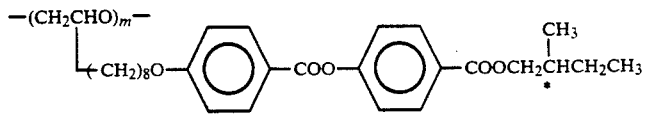

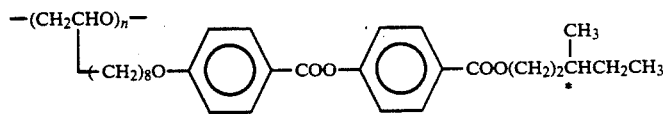

8.(1) Synthesis of 3-methylpentyl p-hydroxybenzoate 13.7 g of p-hydroxybenzoic acid and 11.4 g of (S)-(+)-3-methyl-1-pentanol were refluxed for 10 hours in toluene in the presence of sulfuric acid, while removing out the generated water from the reaction system. Subsequently, the reaction solution was washed with water to remove the sulfuric acid out. The reaction solution was then dried, concentrated, and purified by column chromatography, to obtain 17.8 g of the objective ester compound (liquid state at room temperature ($[\alpha]_d^{23} = +7.8°$ (CHCl$_3$)). (Yield: 80%)

8.(2) Synthesis of 3-methylpentyl 4-[4'-(9-decenyloxy)benzoyloxy]benzoate

To 5.5 g of 4-(9-decenyloxy)benzoic acid prepared in the same manner as in 1.(2) in Example 1 added was toluene, and the mixture was cooled in an ice bath. During cooling of the mixture in an ice bath, 7.0 g of thionyl chloride was added to the mixture. After conclusion of dropping, reaction was carried out for 7 hours at 80° C. After conclusion of the reaction, the reaction solution was concentrated to obtain an acid chloride compound. While, 4.5 g of 3-methylpentyl 4-hydroxybenzoate obtained in 8.(1) and 1.8 g of pyridine were dissolved in toluene, and the resulting toluene solution was cooled in an ice bath. Added dropwise thereto was a toluene solution of the above-described acid chloride compound. After conclusion of dropping, reaction was carried out for 5 hours at 50° C. After conclusion of the reaction, the product was washed with water and dried over magnesium sulfate, to obtain 7.9 g of the objective alkene compound ($[\alpha]_D^{23} = +4.4°$ (CHCl$_3$)). (Yield: 86%)

8.(3) Epoxidation 4.8 g of the alkene compound obtained in 8.(2) was subjected to the same procedure as in 1.(3) in Example 1, to obtain 4.9 g of a monomer (L configuration) represented by the following formula. (Yield: 99%)

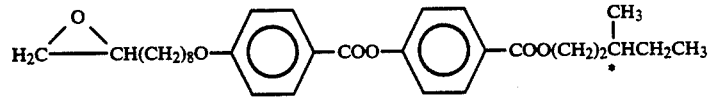

8.(4) Synthesis of Polymer

After a stream of gaseous argon was passed through a solution of 0.8 mmol (0.39 g) of the monomer synthesized in 1.(6) in Example 1 and 1.2 mmol (0.60 g) of the monomer synthesized in 8.(3) dissolved in 10 ml of methylene chloride to displace the air in the solution and reaction apparatus, 0.20 mmol of stannic chloride was added to the solution, and the mixture was then allowed to stand for 5 days at room temperature. After concentration of the reaction solution, the concentrate was purified by column chromatography, to obtain 0.70 g of a polymer. (conversion rate: 71%, Mn=3,000, copolymerization ratio m:n according to NMR spectrum=43:57)

The helical pitches, phase transition behaviors, and response speeds to electric field of the polymers obtained in the above-described Examples 1 to 8 and Comparative examples 1 and 2 were shown in Table 1.

EXAMPLE 9

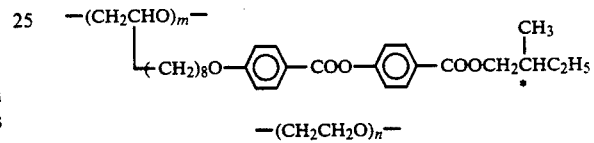

9.(1) Synthesis of 2-methylbutyl 4-hydroxybenzoate 4.0 g of p-hydroxybenzoic acid and 12.5 g of (−)-2-methylbutanol were refluxed for 6 hours in toluene in the presence of sulfuric acid, while removing the generated water out from the reaction system. Subsequently, the reaction solution was washed with water to remove sulfuric acid out. The reaction solution was then dried and concentrated, and the concentrate was purified by column chromatography, to obtain 5.0 g of the objective ester compound (liquid state at room temperature, $[\alpha]_D^{23} = 4.9°$ (CHCl$_3$)). (Yield: 83%)

9.(2) Synthesis of 2-methylbutyl 4-[4'-(9-decenyloxy)benzoyloxy]benzoate 10.0 g of 10-chloro-1-decene and 25 g of sodium iodide were allowed to react in 2-butanone for 10 hours at 80° C. to replace chloro group with iodo group. After the reaction solution was washed with water and dried, the solvent was removed out from the dried solution. 11.5 g of ethyl p-hydroxybenzoate and 9.6 g of potassium carbonate were then added to the residue, and the mixture was then refluxed in absolute ethanol for 15 hours. After addition of an aqueous potassium hydroxide solution containing 4.0 g of potassium hydroxide, the mixture was further heated at 80° C. for 5 hours. After conclusion of the reaction, the reaction solution was acidified with hydrochloric acid and then concentrated under reduced pressure. Water was added to the residue to obtain a suspension, and insoluble matter in the suspension was collected from the suspension and dried, to obtain 9.5 g of 4-(9-decenyloxy)benzoic acid. (Yield: 60%) To 4.5 g of the obtained 4-(9-decenyloxy)-benzoic acid added was toluene, and the resulting toluene solution was cooled in an ice bath. During cooling of the toluene solution in the ice bath, 3.5 g of thionyl chloride was added dropwise thereto. After conclusion of dropping, reaction was carried out for 7 hours at 80° C. After conclusion of the reaction, the reaction solution was concentrated to obtain an acid chloride compound. While, 4.5 g of 2-methylbutyl 4-hydroxybenzoate obtained in 9.(1) and 1.8 g of pyridine were dissolved in toluene, and the resulting toluene solution was cooled in an ice bath. Added dropwise thereto was a toluene solution of the above-described acid chloride compound. After conclusion of dropping the toluene solution, the reaction was carried out for 5 hours at 50° C. After conclusion of the reaction, the product was washed with water and dried over magnesium sulfate, and the dried matter was purified by column chromatography, to obtain 5.5 g of the objective alkene compound. (Yield: 72%)

9.(3) Epoxidation

After a stream of gaseous argon was passed through a solution of 5.5 g of the alkene compound obtained in 9.(2) and 3 mmol (0.52 g) of m-chloroperbenzoic acid dissolved in 10 ml of methylene chloride to displace the air in the solution and reaction apparatus, the solution was stirred for 10 hours. The reaction solution was then washed with an aqueous solution of potassium carbonate, dried, and concentrated, to obtain 5.2 g of a monomer represented by the following formula. (Yield: 92%)

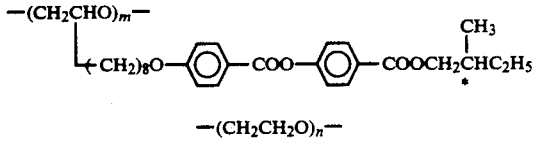

9.(4) Synthesis of Polymer

After a stream of gaseous argon was passed through a solution of 2.0 mmol (0.96 g) of the monomer synthesized in 9.(3) dissolved in 10 ml of methylene chloride to displace the air in the solution and reaction apparatus, 0.5 mmol (22 mg) of ethylene oxide and 0.25 mmol of stannic chloride were added to the solution, and the mixture was then allowed to stand for 5 days at room temperature. After concentration of the reaction solution, the concentrate was purified by column chromatography, to obtain 0.70 g of a polymer (conversion rate: 71%, Mn=2,200, copolymerization ratio m:n according to NMR spectrum=77:23).

EXAMPLE 10

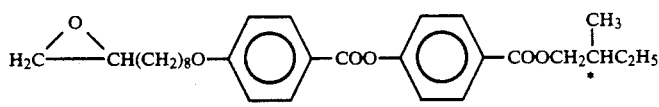

10.(1) Synthesis of Polymer

After a stream of gaseous argon was passed through a solution of 2.0 mmol (0.96 g) of the monomer synthesized in 9.(3) in Example 9 dissolved in 10 ml of methylene chloride to displace the air in the solution and reaction apparatus, 2.0 mmol (0.09 g) of ethylene oxide and 0.40 mmol of stannic chloride were added to the solution, and the mixture was allowed to stand for 5 days at room temperature. After concentration of the reaction solution, the concentrate was purified by column chromatography, to obtain 0.64 g of a polymer (conversion rate: 64%, Mn=1,700, copolymerization ration m:n according to NMR spectrum=54:46).

EXAMPLE 11

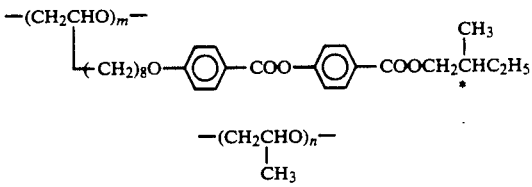

11.(1) Synthesis of Polymer

After a stream of gaseous argon was passed through a solution of 2.0 mmol (0.96 g) of the monomer synthesized in 9.(3) in Example 9 dissolved in 10 ml of methylene chloride to displace the air in the solution and reaction apparatus, 2.0 mmol (0.12 g) of propylene oxide and 0.40 mmol of stannic chloride were added to the solution, and the mixture was allowed to stand for 5 days at room temperature. After concentration of the reaction solution, the concentrate was purified by column chromatography, to obtain 0.71 g of a polymer (conversion rate: 72%, Mn=1,600, copolymerization ratio m:n according to NMR spectrum=60:40).

EXAMPLE 12

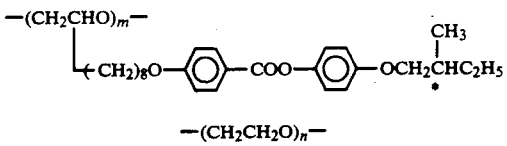

12.(1) Synthesis of 4-(2-methylbutoxy)phenol

Into a n-butanol suspension containing 37 mmol (9.0 g) of 2-methylbutyl p-toluenesufonate prepared by tosylating S-(—)-2-methylbutanol and 74 mmol (8.2 g) of hydroquinone, added dropwise was a solution of 50 mmol (2.1 g) of sodium hydroxide dissolved in a solvent mixture of 3 ml of water and 10 ml of n-butanol. After conclusion of the dropping, the mixture was then stirred for 8 hours at 120° C. After addition of water, the reaction solution was extracted with ether, and the extracted solution was dried and concentrated. The concentrate was purified by column chromatography, to obtain 4.8 g of the objective ether compound (Yield: 72%)

12.(2) Synthesis of 4-(2-methylbutoxy)phenyl 4-(9-decenyloxy)benzoate 10.0 g of 10-chloro-1-decene and 25 g of sodium iodide were allowed to react in 2-butanone for 10 hours at 80° C., to replace the chloro group with iodo group. After the resulting product was washed with water and dried, the solvent was removed out from the dried product. To the resulting residue added were 11.5 g of ethyl p-hydroxybenzoate and 9.6 g of potassium carbonate, and the mixture was then refluxed for 15 hours in an absolute ethanol. After addition of an aqueous potassium hydroxide solution containing 4.0 g of potassium hydroxide, the mixture was further heated for 5 hours at 80° C. After conclusion of the reaction, the reaction solution was acidified with hydrochloric acid and was then concentrated under reduced pressure. Water was added to the residue to obtain a suspention, and the insoluble matter in the suspension was collected from the suspension and was dried, to obtain 9.5 g of 4-(9-decenyloxy)benzoic acid. (Yield: 60%)

Subsequently, a toluene solution containing 10 mmol (2.8 g) of 4-(9-decenyloxy)benzoic acid and 30 mmol (3.6 g) of thionyl chloride dissolved was allowed to react for 3 hours at 100° C. and was then concentrated under reduced pressure, to obtain an acid chloride compound. After a solution of the acid chloride compound dissolved in 5 ml of THF was added dropwise into a solution of 8 mmol (1.4 g) of the ether compound obtained in 12.(1) and 2 ml of triethylamine dissolved in 20 ml of THF, the resulting mixture was stirred for 10 hours. After addition of water, the reaction solution was extracted with ether, and the extracted solution was dried and concentrated. The concentrate was purified by column chromatography to obtain 2.2 g of the objective alkene compound. (Yield: 63%)

12.(3) Epoxidation

After a stream of gaseous argon was passed through a solution of 2 mmol (0.84 g) of the alkene compound obtained in 12.(2) and 3 mmol (0.52 g) of m-chloroperbenzoic acid dissolved in 10 ml of methylene chloride to displace the air in the solution and the reaction apparatus, the solution was stirred for 10 hours. After the reaction solution was washed with an aqueous potassium carbonate solution, the washed reaction solution was dried and concentrated, to obtain 0.82 g of a monomer represented by the following formula. (Yield: 90%)

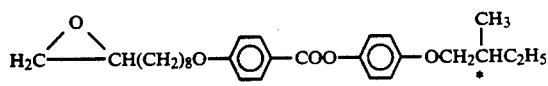

12.(4) Synthesis of Polymer

After a stream of gaseous argon was passed through a solution of 2.0 mmol (0.91 g) of the monomer synthesized in 12.(3) dissolved in 10 ml of methylene chloride to displace the air in the solution and the reaction apparatus, 0.5 mmol (22 mg) of etylene oxide and 0.25 mmol of stannic chloride were added to the solution, and the mixture was then allowed to stand for 5 days at room temperature. After concentration of the reaction solution, the concentrate was purified by column chromatography, to obtain 0.59 g of a polymer (conversion rate: 63%, $Mn=2,600$, copolymerization ratio m:n according to NMR spectrum=88:12).

EXAMPLE 13

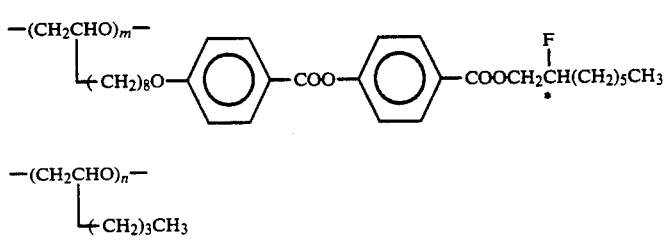

13.(1) Synthesis of 2-fluorooctyl p-hydroxybenzoate

To 5.4 g of p-acetoxybenzoic acid added dropwise was 11 g of thionyl chloride. The resulting mixture was heated to 80° C. and then allowed to react for 3 hours. After conclusion of the reaction, the excessive thionyl chloride was distilled out from the reaction solution under reduced pressure, to obtain an acid chloride compound. The acid chloride compound was dissolved in toluene and the resulting solution was cooled in an ice bath. Added dropwise thereto was a toluene solution containing 4.4 g of (−)-2-fluorooctanol and 3 g of pyridine. The obtained mixture was stirred overnight at room temperature. After conclusion of the reaction, the reaction solution was washed with water, dried, and concentrated under reduced pressure. The residue was dissolved in ether. 10 g of benzylamine was added dropwise to the ether solution. The resulting mixture was stirred for 5 hours at room temperature. After conclusion of the reaction, the product was washed with water, dried, and concentrated under reduced pressure. The residue was purified by column chromatography, to obtain 4.9 g of the objective ester compound. (Yield: 73%)

13.(2) Synthesis of 2-fluorooctyl 4-[4'-(9-decenyloxy)benzoyloxy]benzoate

To 3.0 g of 4-(9-decenyloxy)benzoic acid prepared in the same manner as in 9.(2) in Example 9 added was toluene, and the mixture was cooled in an ice bath. 2.0 g of thionyl chloride was added dropwise to the mixture. Subsequently, reaction was carried out for 3 hours at 80° C. After conclusion of the reaction, the product was concentrated to obtain an acid chloride compound. While, 1.7 g of 2-fluorooctyl 4-hydroxybenzoate and 0.9 g of pyridine were dissolved in toluene, and the resulting solution was cooled in an ice bath. Added dropwise thereto was a toluene solution of the above-described acid chloride compound. Reaction was then carried out for 15 hours at room temperature. After conclusion of the reaction, the product was washed with water and dried over magnesium sulfate, and the solvent was then distilled out from the dried product under reduced pressure. The residue was purified by column chromatography to obtain 2.8 g of the objective ester compound. (Yield: 85%)

13.(3) Epoxidation 2.8 g of the ester compound obtained in 13.(2) was subjected to the same procedure as in 9.(3) in Example 9, to obtain 2.6 g of a monomer represented by the following formula. (Yield: 91%)

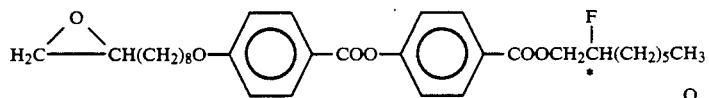

13.(4) Synthesis of Polymer

After a stream of gaseous argon was passed through a solution of 2.0 mmol (1.08 g) of the monomer synthesized in 13.(3) dissolved in 10 ml of methylene chloride to displace the air in the solution and the reaction apparatus, 0.5 mmol (50 mg) of 1,2-epoxyhexane and 0.25 mmol of stannic chloride were added to the solution, and the mixture was then allowed to stand for 5 days at room temperature. After concentration of the reaction solution, the concentrate was purified by column chromatography, to obtain 0.88 g of a polymer (conversion rate: 78%, $Mn=2,400$, copolymerization ratio m:n according to NMR spectrum$=82:18$).

EXAMPLE 14 tography to obtain 4.3 g of the objective ester compound. (Yield: 80%)

14.(2) Epoxidation 4.3 g of the ester compound obtained in 14.(1) was subjected to the same procedure as in 9.(3) in Example 9, to obtain 4.2 g of a monomer represented by the following formula. (Yield: 95%)

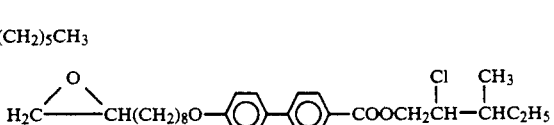

14.(3) Synthesis of Polymer

After a stream of gaseous argon was passed through a solution of 2.0 mmol (0.97 g) of the monomer synthesized in 14.(2) to displace the air in the solution and the reaction apparatus, 0.5 mmol (22 mg) of ethylene oxide and 0.25 mmol of stannic chloride were added to the solution, and the resulting mixture was allowed to stand for 5 days at room temperature. After the reaction solution was concentrated, the concentrate was purified by column chromatography, to obtain 0.58 g of a polymer (conversion rate: 58%, $Mn=2,400$, copolymerization ratio m:n according to NMR spectrum$=84:16$).

EXAMPLE 15

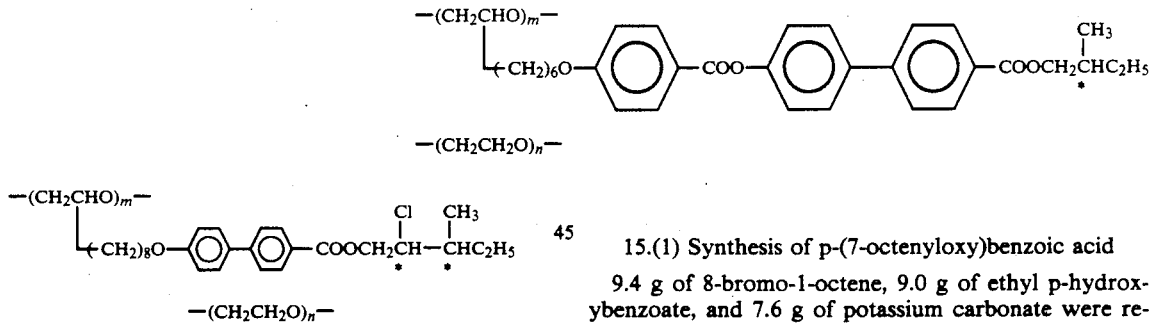

14.(1) Synthesis of 2-chloro-3-methylpentyl 4'-(9-decenyloxy)biphenyl-4-carboxylate To 4.0 g of 4'-(9-decenyloxy)biphenyl-4-carboxylic acid was added toluene, and the mixture was cooled in an ice bath. Added dropwise thereto was 2.0 g of thionyl chloride. Reaction was then carried out for 7 hours at 80° C. After conclusion of the reaction, the reaction solution was concentrated to obtain an acid chloride compound. 1.7 g of 2-chloro-3-methylpentanol and 1.0 g of pyridine were dissolved in toluene, and the solution was cooled in an ice bath. Added dropwise thereto was a toluene solution of the above-described acid chloride compound. Reaction was then carried out for 15 hours at room temperature. After conclusion of the reaction, the reaction solution was washed with water and dried over magnesium sulfate, and the solvent was distilled out from the dried reaction solution under reduced pressure. The residue was purified by column chroma-

15.(1) Synthesis of p-(7-octenyloxy)benzoic acid 9.4 g of 8-bromo-1-octene, 9.0 g of ethyl p-hydroxybenzoate, and 7.6 g of potassium carbonate were refluxed in ethanol for 10 hours. Added thereto was an aqueous solution containing 2.4 g of sodium hydroxide, and reflux was further continued for 10 hours. After conclusion of the reaction, the reaction solution was diluted with water, and the pH of the diluted solution was lowered to 2 by dropping hydrochloric acid thereto. The generated precipitate was collected, and was then washed with water sufficiently and dried, to obtain 10.8 g of the objective ether compound. (Yield: 89%)

15.(2) Synthesis of 2-methylbutyl 4-[p-(7-octenyloxy)benzoyloxy]biphenyl-4-carboxylate 9 g of p-(7-octenyloxy)benzoic acid obtained in 15.(1) was suspended in toluene, and the suspension was cooled in an ice bath. Added dropwise thereto was 6 g of thionyl chloride. After conclusion of the dropping, the temperature was raised and reaction was carried out for 6 hours at 80° C. After conclusion of the reaction, the reaction solution was concentrated under reduced pressure, to obtain an acid chloride compound. Toluene was added to the acid chloride compound, and the resulting toluene solution was cooled in an ice bath. A toluene solution containing 10 g of 2-methylbutyl 4'-hydroxybiphenyl-4-carboxylate and 3 g of pyridine was added dropwise into the above-described toluene solution of the acid chloride compound. After conclusion of dropping, the temperature was raised, and reaction was carried out for 8 hours at 50° C. After conclusion of the reaction, the product was washed with water, dried over magnesium sulfate, and concentrated under reduced pressure. The residue was recrystallized from ethanol, to obtain 8.2 g of the objective ester compound. (Yield: 45%)

15.(3) Epoxidation 7.2 g of the ester compound obtained in 15.(2) was acidified with 3 g of m-chloroperbenzoic acid, to obtain 6.3 g of a monomer represented by the following formula. (Yield: 85%)

cooled in an ice bath. 2.6 g of thionyl chloride was added dropwise to the mixture. Subsequently, reaction was carried out for 7 hours at 80° C. After conclusion of the reaction, the product was concentrated to obtain an acid chloride compound. 3.1 g of 2-methylbutyl 4-hydroxybenzoate prepared in the same manner as in 9.(1) in Example 9 and 1.5 g of pyridine were dissolved in toluene, and the toluene solution was cooled in an ice bath. Added dropwise thereto was a toluene solution of the above-described acid chloride compound. Subsequently, reaction was carried out for 5 hours at 50° C. After conclusion of the reaction, the product was washed with water and dried over magnesium sulfate, and the solvent was distilled out from the dried product under reduced pressure. The residue was purified by column chromatography to obtain 5.2 g of the objective ester compound. (Yield: 68%)

16.(2) Epoxidation 5.2 g of the ester compound obtained in 16.(1) was subjected to the same procedure as in 9.(3) in Example 9, to obtain 4.9 g of a monomer represented by the following formula. (Yield: 92%)

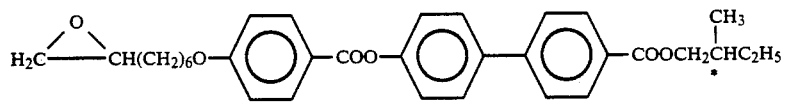

15.(4) Synthesis of Polymer

After a stream of gaseous argon was passed through an solution of 2.0 mmol (1.06 g) of the monomer synthesized in 15.(3) dissolved in 10 ml of methylene chloride to displace the air in the solution and the reaction apparatus, 2.0 mmol (0.09 g) of ethylene oxide and 0.40 mmol of stannic chloride were added to the solution, and the mixture was then allowed to stand for 5 days at room temperature. After concentration of the reaction solution, the concentrate was purified by column chromatography, to obtain 0.74 g of a polymer (conversion rate: 64%, Mn=2,200, copolymerization ratio m:n according to NMR spectrum=80:20).

EXAMPLE 16

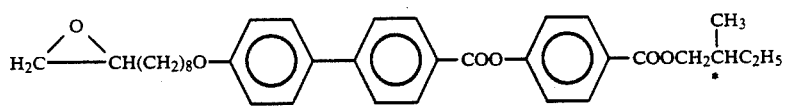

16.(3) Synthesis of Polymer

After a stream of gaseous argon was passed through a solution of 2.0 mmol (1.12 g) of the monomer synthesized in 16.(2) dissolved in 10 ml of methylene chloride to displace the air in the solution and the reaction apparatus, 2.0 mmol (0.09 g) of ethylene oxide and 0.40 mmol of stannic chloride were added to the solution, and the mixture was then allowed to stand for 5 days at room temperature. After concentration of the reaction solution, the concentrate was purified by column chromatography, to obtain 0.73 g of a polymer (conversion rate: 60%, Mn=2,100, copolymerization ratio m:n according to NMR spectrum=78:22).

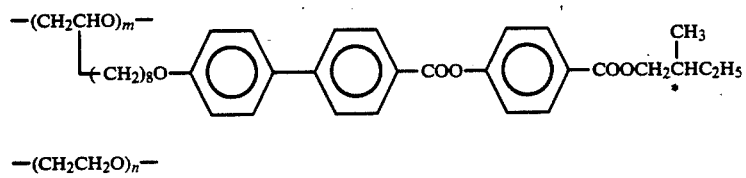

16.(1) Synthesis of 2-methylbutyl 4[4'-(9-decenyloxy)biphenylyl-4-carbonyloxy]benzoate To 5.0 g of 4'-(9-decenyloxy)biphenyl-4-carboxylic acid added was toluene, and the mixture was then

EXAMPLE 17

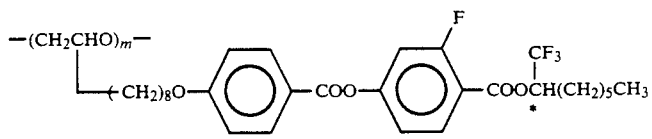

17.(1) Synthesis of 1-trifluoromethylheptyl 4-hydroxy-2-fluorobenzoate

A solution of 20 mmol (4.0 g) of 4-acetoxy-2-fluorobenzoic acid and 60 mmol (7.2 g) of thionyl chloride dissolved in 100 ml of toluene was stirred for 2 hours at 80° C., and the reaction solution was concentrated under reduced pressure, to obtain an acid chloride compound. A solution of the acid chloride compound dissolved in 10 ml of THF was added dropwise to a solution of 15 mmol (2.8 g) of R-(+)-1,1,1-trifluoro-2-octanol and 5 ml of triethylamine dissolved in 30 ml of THF, and the mixture was then stirred for 10 hours. After concentration of the reaction solution, water was added to the concentrate, and the mixture was then extracted with ether. After concentration of the extracted solution, the concentrate was dissolved in 200 ml of ether. To the resulting ether solution added was 20 ml of benzylamine, and the mixture was stirred for 5 hours. The reaction solution was washed with water and was then purified by column chromatography, to obtain 2.5 g of the objective hydroxy compound. (Yield: 52%)

17.(2) Synthesis of 1-trifluoromethylheptyl 4-[4'-(9-decenyloxy)benzoyloxy]-2-fluorobenzoate To 2.8 g of p-(9-decenyloxy)benzoic acid prepared in the same manner as in 9.(2) in Example 9 added was toluene, and the resulting mixture was cooled in an ice bath. 5.0 g of thionyl chloride was then added dropwise to the toluene solution. Reaction was then carried out for 7 hours at 80° C. After conclusion of the reaction, the reaction solution was concentrated under reduced pressure, to obtain crude p-decenyloxybenzoyl chloride. 1.6 g of the hydroxy compound obtained in 17.(1) and 3.3 g of pyridine were dissolved in toluene, and the resulting toluene solution was cooled in an ice bath. A toluene solution containing the above crude p-decenyloxybenzoyl chloride was added dropwise into the toluene solution. Subsequently, reaction was carried out for 5 hours at 50° C. After conclusion of the reaction, the reaction solution was washed with water and dried over magnesium sulfate, and the solvent was distilled out under reduced pressure. The residue was purified by column chromatography, to obtain 2.0 g of the objective alkene compound. (Yield: 69%)

17.(3) Epoxidation

A monomer represented by the following formula was synthesized in the same manner as in 9.(3) in Example 9 using 2.0 mmol (1.16 g) of the alkene compound obtained in 17.(2) as the raw material. (Yield: 86%)

17.(4) Synthesis of Polymer

The same procedure as in 11.(1) in Example 11 was repeated with the exception that 1.0 mmol (600 mg) of the monomer obtained in 17.(3) and 0.5 mmol (29 mg) of propylene oxide were used as the raw materials, to synthesize a polymer (conversion rate: 78%, Mn=2,000, copolymerization ratio m:n according to NMR spectrum=70:30).

EXAMPLE 18

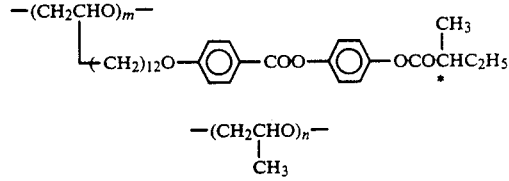

18.(1) Synthesis of 4-(2-methylbutanoyloxy)phenol

Into a solution of 50 mmol (5.1 g) of S-(+)-2-methylbutanoic acid and 100 mmol (11.0 g) of hydroquinone dissolved in 150 ml of toluene added was 1 ml of concentrated sulfuric acid, and the mixture was then refluxed for 3 hours with stirring. After concentration of the reaction solution, the concentrate was purified by column chromatography, to obtain 7.1 g of the objective hydroxy compound. (Yield: 73%)

18.(2) Synthesis of 4'-(2-methylbutanoyloxy)phenyl 4-(13-tetradecenyloxy)benzoate The procedure as in 12.(2) in Example 12 was repeated with the exception that 15 mmol (5.0 g) of 4-(13-tetradecenyloxy)benzoic acid and 10 mmol (1.9 g) of the hydroxy compound obtained in 18.(1) were used as the raw materials, to synthesize the objective alkene compound. (Yield: 80%)

18.(3) Epoxidation

The procedure as in 12.(3) in Example 12 was repeated with the exception that 2.0 mmol (1.0 g) of the alkene compound obtained in 18.(2) was used as the raw material. (Yield: 93%)

18.(4) Synthesis of Polymerization

The procedure as in 11.(1) in Example 11 was repeated with the exception that 1.0 mmol (510 mg) of the monomer obtained in 18.(3) and 0.5 mmol (29 mg) of propylene oxide were used as the raw materials, to synthesize a polymer (conversion rate: 78%,

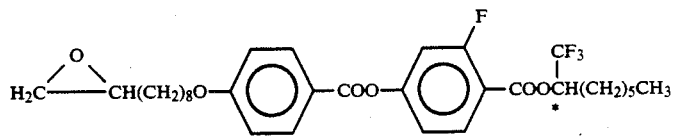

Mn=2,200, copolymerization ratio m:n according to NMR spectrum=72:28).

COMPARATIVE EXAMPLE 3

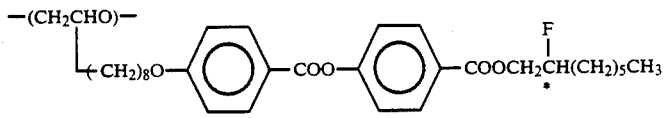

(1) Synthesis of Polymer

The polymer having the repeating unit represented by the above formula was synthesized by using the monomer synthesized in 13.(3) in Example 13, in the same manner as in Example 9. (conversion rate: 63%, Mn=2,700)

COMPARATIVE EXAMPLE 4

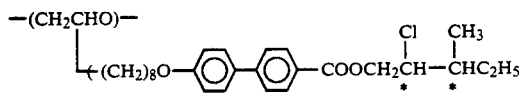

(1) Synthesis of Polymer

The polymer having the repeating unit represented by the above formula was synthesized by using the monomer synthesized in 14.(2) in Example 14, in the same manner as in Example 9. (conversion rate: 75%, Mn=2,900)

COMPARATIVE EXAMPLE 5

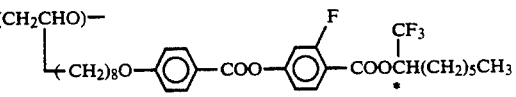

(1) Synthesis of Polymer

The polymer having the repeating unit represented by the above formula was synthesized by using the monomer synthesized in 17.(3) in Example 17, in the same manner as in Example 9. (conversion rate: 83%, Mn=2,100)

The phase transition behaviors, helical pitches, and response speeds to electric field of the polymers obtained in Examples 9 to 18 and Comparative Examples 3 to 5 are shown in Table 2.

TABLE 1

| | Repeating Unit | Copolymerization ratio | Phase transition behavior (°C.) | Helical Pitch (μm) | Response time (ms) | Measuring temperature (°C.) |
|---|---|---|---|---|---|---|
| Example 1 | —(CH₂CHO)ₘ— with side chain —(CH₂)₈O—⟨○⟩—COO—⟨○⟩—COO—⟨○⟩—COOCH₂CHC₂H₅ / CH₃ *<br>—(CH₂CHO)ₙ— with side chain —(CH₂)₈O—⟨○⟩—COO—⟨○⟩—COO—⟨○⟩—OCH₂CHC₂H₅ / CH₃ * | m:n = 58:42 | g $\xrightarrow{-8}_{-10}$ SmC* $\xrightarrow{56}_{53}$ SmA $\xrightarrow{74}_{70}$ Iso | 4.2 | 25 (45), 30 (30), 70 (15) | |
| Example 2 | —(CH₂CHO)ₘ— with side chain —(CH₂)₈O—⟨○⟩—COO—⟨○⟩—COO—⟨○⟩—COOCH₂CHC₂H₅ / CH₃ *<br>—(CH₂CHO)ₙ— with side chain —(CH₂)₈O—⟨○⟩—COO—⟨○⟩—COO—⟨○⟩—COOCH₂CH(CH₂)₅CH₃ / F * | m:n = 60:40 | SmI $\xrightarrow{-4}_{-6}$ SmC* $\xrightarrow{49}_{46}$ SmA $\xrightarrow{62}_{58}$ N* $\xrightarrow{63}_{60}$ Iso | 3.8 | 3 (40), 5 (30), 20 (20), 100 (10) | |
| Example 3 | —(CH₂CHO)ₘ— with side chain —(CH₂)₈O—⟨○⟩—COO—⟨○⟩—COO—⟨○⟩—COOCH₂CHC₂H₅ / CH₃ *<br>—(CH₂CHO)ₙ— with side chain —(CH₂)₈O—⟨○⟩—COO—⟨○⟩—COO—⟨○⟩—COOCH—CHCH₃ / CH₃ Cl * | m:n = 75:25 | g $\xrightarrow{7}_{0}$ SmC* $\xrightarrow{65}_{62}$ SmA $\xrightarrow{98}_{94}$ Iso | 2.5 | 10 (60), 100 (10) | |
| Example 4 | —(CH₂CHO)ₘ— with side chain —(CH₂)₆O—⟨○⟩—COO—⟨○⟩—COO—⟨○⟩—COOCH₂CHC₂H₅ / CH₃ *<br>—(CH₂CHO)ₙ— with side chain —(CH₂)₈O—⟨○⟩—COO—⟨○⟩—COO—⟨○⟩—OCH₂CHC₂H₅ / CH₃ * | m:n = 25:75 | g $\xrightarrow{8}_{4}$ SmC* $\xrightarrow{73}_{70}$ SmA $\xrightarrow{100}_{97}$ N* $\xrightarrow{103}_{101}$ Iso | 2.8 | 48 (65) | |

TABLE 1-continued

| | Repeating Unit | Copolymerization ratio | Phase transition behavior (°C.) | Helical Pitch (μm) | Response time (ms) Measuring temperature (°C.) |
|---|---|---|---|---|---|
| Example 5 | −(CH$_2$CHO)$_m$− with phenyl-COO-phenyl(F)(CF$_3$)-COOCH(CH$_2$)$_5$CH$_3$* attached via −(CH$_2$)$_8$O−; −(CH$_2$CHO)$_n$− with phenyl-COO-phenyl-OCH$_2$CHC$_2$H$_5$(CH$_3$)* attached via −(CH$_2$)$_8$O− | m:n = 48:52 | g $\xrightarrow{-10}_{-13}$ SmC* $\xrightarrow{39}_{37}$ SmA $\xrightarrow{55}_{52}$ Iso | 4.8 | 9 (30) |
| Example 6 | −(CH$_2$CHO)$_m$− with phenyl-COO-phenyl-COOCH$_2$CHC$_2$H$_5$(CH$_3$)* attached via −(CH$_2$)$_8$O−; −(CH$_2$CHO)$_n$− with phenyl-COO-phenyl-OCOCH$_2$C$_2$H$_5$(CH$_3$)* attached via −(CH$_2$)$_{12}$O− | m:n = 55:45 | g $\xrightarrow{3}_{0}$ SmC* $\xrightarrow{51}_{50}$ SmA $\xrightarrow{64}_{62}$ Iso | 3.4 | 24 (45) |
| Example 7 | −(CH$_2$CHO)$_m$− with phenyl-COO-phenyl-COOCH$_2$CHC$_2$H$_5$(CH$_3$)* attached via −(CH$_2$)$_8$O−; −(CH$_2$CHO)$_n$− with phenyl-COO-phenyl-COOCH(CH$_2$)$_2$CH$_3$(CH$_3$)* attached via −(CH$_2$)$_8$O− | m:n = 38:62 | g $\xrightarrow{-13}_{-16}$ SmC* $\xrightarrow{24}_{22}$ SmA $\xrightarrow{37}_{33}$ Iso | 3.5 | 2 (20) / 20 (10) |
| Example 8 | −(CH$_2$CHO)$_m$− with phenyl-COO-phenyl-COOCH$_2$CHC$_2$H$_5$(CH$_3$)* attached via −(CH$_2$)$_8$O−; −(CH$_2$CHO)$_n$− with phenyl-COO-phenyl-COO(CH$_2$)$_2$CHCH$_2$CH$_3$(CH$_3$)* attached via −(CH$_2$)$_8$O− | m:n = 43:57 | g $\xrightarrow{3}_{1}$ SmC* $\xrightarrow{37}_{35}$ SmA $\xrightarrow{50}_{45}$ Iso | 4.5 | 15 (30) / 300 (10) |
| Comparative Example 1 | −(CH$_2$CHO)− with phenyl-COO-phenyl-COOCH$_2$CHC$_2$H$_5$(CH$_3$)* attached via −(CH$_2$)$_8$O− | | g $\xrightarrow{-20}_{-24}$ SmI $\xrightarrow{4}_{0}$ SmC* $\xrightarrow{38}_{36}$ SmA $\xrightarrow{58}_{54}$ Iso | 2.0 | 10 (30) |
| Comparative Example 2 | −(CH$_2$CHO)− with phenyl-COO-phenyl-OCH$_2$CHC$_2$H$_5$(CH$_3$)* attached via −(CH$_2$)$_8$O− | | SmI $\xrightarrow{24}_{17}$ SmC* $\xrightarrow{40}_{37}$ SmA $\xrightarrow{63}_{61}$ Iso | 1.8 | 90 (30) |

TABLE 2

| | Repeating unit | Copolymerization ratio | Phase transition behavior (°C.) | Helical pitch (μm) | Response time (ms) (Measuring temperature (°C.)) |
|---|---|---|---|---|---|
| Example 9 | —(CH$_2$CHO)$_m$— with —(CH$_2$)$_8$O—⬡—COO—⬡—COOCH$_2$CHC$_2$H$_5$ (CH$_3$, *); —(CH$_2$CH$_2$O)$_n$— | m:n = 77:23 | g $\xrightarrow{-24}_{-25}$ SmC* $\xrightarrow{27}_{25}$ SmA $\xrightarrow{54}_{52}$ Iso | 4.2 | 2 (20) |
| Example 10 | —(CH$_2$CHO)$_m$— with —(CH$_2$)$_8$O—⬡—COO—⬡—COOCH$_2$CHC$_2$H$_5$ (CH$_3$, *); —(CH$_2$CH$_2$O)$_n$— | m:n = 54:46 | g $\xrightarrow{-30}_{-33}$ SmC* $\xrightarrow{-2}_{-5}$ SmA $\xrightarrow{32}_{31}$ Iso | 2.4 | 4 (−10) |
| Example 11 | —(CH$_2$CHO)$_m$— with —(CH$_2$)$_8$O—⬡—COO—⬡—COOCH$_2$CHC$_2$H$_5$ (CH$_3$, *); —(CH$_2$CH$_2$O)$_n$—CH$_3$ | m:n = 60:40 | g $\xrightarrow{-22}_{-25}$ SmC* $\xrightarrow{30}_{28}$ SmA $\xrightarrow{60}_{57}$ Iso | 3.4 | 2 (25) |
| Example 12 | —(CH$_2$CHO)$_m$— with —(CH$_2$)$_8$O—⬡—COO—⬡—OCH$_2$CHC$_2$H$_5$ (CH$_3$, *); —(CH$_2$CH$_2$O)$_n$— | m:n = 88:12 | g $\xrightarrow{-12}_{-15}$ SmC* $\xrightarrow{28}_{25}$ Iso | 2.2 | 4 (20) |
| Example 13 | —(CH$_2$CHO)$_m$— with —(CH$_2$)$_8$O—⬡—COO—⬡(F)—COOCH$_2$CH(CH)$_5$CH$_3$ (*); —(CH$_2$CH$_2$O)$_n$—(CH$_2$)$_3$CH$_3$ | m:n = 82:18 | g $\xrightarrow{33}$ SmA $\xrightarrow{44}_{42}$ N* $\xrightarrow{47}_{44}$ Iso; $\searrow$ 5 SmC* $\nearrow$ 28 | 1.8 | 1 (25) |
| Example 14 | —(CH$_2$CHO)$_m$— with —(CH$_2$)$_8$O—⬡—COO—⬡(Cl)—COOCH$_2$CH—CHC$_2$H$_5$ (CH$_3$, *); —(CH$_2$CH$_2$O)$_n$— | m:n = 84:16 | g $\xrightarrow{4}_{0}$ SmC* $\xrightarrow{55}_{51}$ SmA $\xrightarrow{68}_{66}$ Iso | 1.8 | 1 (45) |

TABLE 2-continued

| | Repeating unit | Copolymerization ratio | Phase transition behavior (°C.) | Helical pitch (μm) | Response time (ms) (Measuring temperature (°C.)) |
|---|---|---|---|---|---|
| Example 15 | —(CH$_2$CHO)$_m$— / ({CH$_2$})$_6$O—[structure]—COO—[structure]—COOCH$_2$CHC$_2$H$_5$ / CH$_3$ / —(CH$_2$CH$_2$O)$_n$— | m:n = 80:20 | g $\xrightarrow{32}_{28}$ SmC* $\xrightarrow{134}_{130}$ N* $\xrightarrow{154}_{151}$ Iso | 2.4 | 12 (60) |
| Example 16 | —(CH$_2$CHO)$_m$— / ({CH$_2$})$_8$O—[structure]—COO—[structure]—COOCH$_2$CHC$_2$H$_5$ / CH$_3$ / —(CH$_2$CH$_2$O)$_n$— | m:n = 78:22 | g $\xrightarrow{20}_{15}$ SmC* $\xrightarrow{83}_{80}$ SmA $\xrightarrow{124}_{123}$ N* $\xrightarrow{130}_{128}$ Iso | 2.5 | 10 (50) |
| Example 17 | —(CH$_2$CHO)$_m$— / ({CH$_2$})$_8$O—[structure F]—COO—[structure]—COOCH(CH$_2$)$_5$CH$_3$ / CF$_3$ / —(CH$_2$CH$_2$O)$_n$—CH$_3$ | m:n = 70:30 | g $\xrightarrow{-31}_{-33}$ SmC* $\xrightarrow{17}_{15}$ SmA $\xrightarrow{32}_{29}$ Iso | 2.0 | 2 (10) |
| Example 18 | —(CH$_2$CHO)$_m$— / ({CH$_2$})$_{12}$O—[structure]—COO—[structure]—OCOCH$_2$C$_2$H$_5$ / CH$_3$ / —(CH$_2$CHO)$_n$—CH$_3$ | m:n = 72:28 | g $\xrightarrow{8}_{5}$ SmC* $\xrightarrow{47}_{47}$ SmA $\xrightarrow{57}_{57}$ Iso | 3.2 | 3 (35) |
| Comparative Example 3 | —(CH$_2$CHO)— / ({CH$_2$})$_8$O—[structure F]—COO—[structure]—COOCH$_2$CH(CH$_2$)$_5$CH$_3$ | | SmI $\xrightarrow{38}_{27}$ SmC* $\xrightarrow{47}_{47}$ N* $\xrightarrow{57}_{57}$ Iso | 1.1 | 2 (35) |
| Comparative Example 4 | —(CH$_2$CHO)— / ({CH$_2$})$_8$O—[structure Cl]—OCH$_2$CH—[structure]—CH$_3$ / CH$_3$ / —CHC$_2$H$_5$ | | SmI $\xrightarrow{12}_{12}$ SmC* $\xrightarrow{65}_{65}$ SmA $\xrightarrow{105}_{84}$ Iso | 1.0 | 2 (40) |
| Comparative Example 5 | —(CH$_2$CHO)— / ({CH$_2$})$_8$O—[structure F]—COO—[structure]—COOCH(CH$_2$)$_5$CH$_3$ / CF$_3$ | | g $\xrightarrow{-2}_{-4}$ SmC* $\xrightarrow{38}_{36}$ SmA $\xrightarrow{54}_{51}$ Iso | 1.5 | 15 (30) |

What is claimed is:
1. A liquid-crystalline copolymer comprising the copolymerization product of;
(a) at least one liquid-crystalline epoxy compound which has a helical structure and is represented by the following general formula (1) and
(b) at least one liquid-crystalline epoxy compound which has a helical structure opposite in twining direction of helix to the helical structure of the liquid-crystalline epoxy compound (a) and is represented by the following general formula (2), the copolymerization product comprising at least one repeating unit represented by the following general formula (3) and at least one repeating unit represented by the following general formula (4), wherein the molar ratio of the repeating unit (3) to the repeating unit (4) is from 99:1 to 1:99;

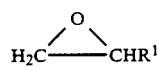 (1)

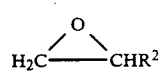 (2)

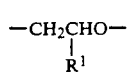 (3)

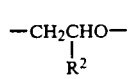 (4)

wherein $R^1$ and $R^2$ are different from each other and each independently are a group represented by $-(CH_2)_k-OR^3$, wherein
k is an integer having a value of from 1 to 30,
$R^3$ is a group represented by $-A_p-X-B_q-R^4$, wherein
X is a single bond, $-COO-$ or $-OCO-$,
p and q each independently are an integer having a value of 1 or 2,
A is

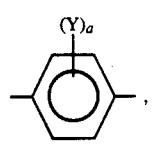

B is

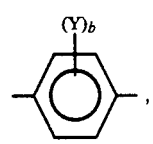

a and b each independently being an integer having a value of from 0 to 4 and being identical with or different from each other, each Y being a halogen atom and being identical with or different from the others,
A and B are identical with or different from each other, and
$R^4$ is $-COOR^5$, $-OCOR^5$ or $-OR^5$, wherein
$R^5$ is

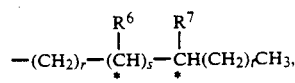

$R^6$ and $R^7$ each independently being $-CH_3$, a halogen atom, $-CN$ or $-CF_3$, r and t each independently being an integer having a value of from 0 to 10, with the proviso that t is not 0 when $R^7$ is $-CH_3$, s being an integer of 0 or 1 and C marked with * is an asymmetric carbon atom.

2. The liquid-crystalline copolymer as claimed in claim 1, wherein k is an integer having a value of from 4 to 16.

3. The liquid-crystalline copolymer as claimed in claim 2, wherein each $R^3$ independently is

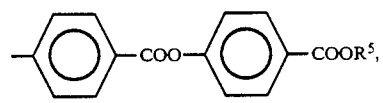

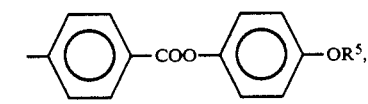

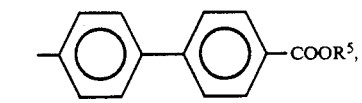

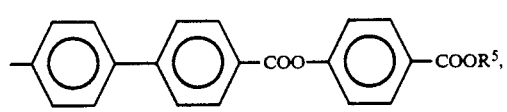

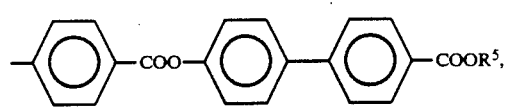

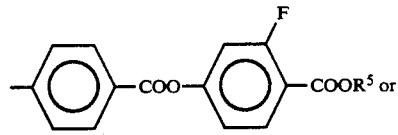

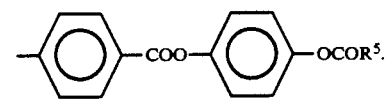

4. The liquid-crystalline copolymer as claimed in claim 3, wherein each $R^5$ independently is

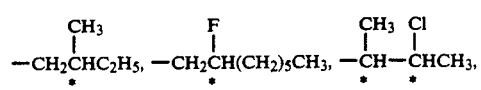

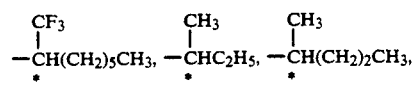

-continued

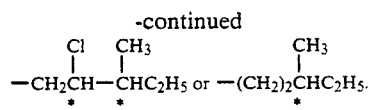

5. The liquid-crystalline copolymer as claimed in claim 2, wherein $R^4$ in $R^1$ is

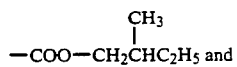

and $R^4$ in $R^2$ is

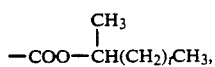

t being an integer having a value of 2 to 5.

6. The liquid-crystalline copolymer as claimed in claim 2, wherein $R^4$ in $R^1$ is

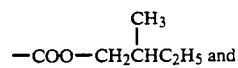

and $R^4$ in $R^2$ is

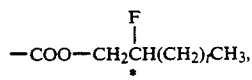

t being an integer having a value of from 3 to 5.

7. The liquid-crystalline copolymer as claimed in claim 1, wherein $R^1$ and $R^2$ each independently are

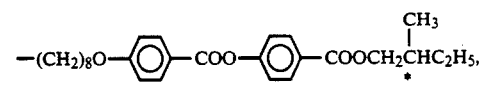
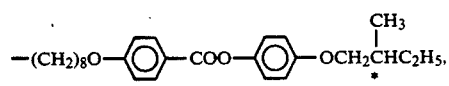
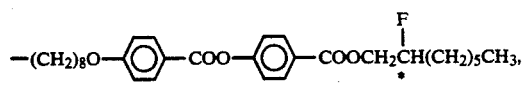
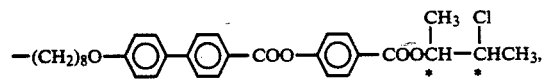
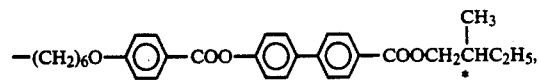
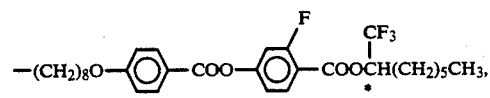
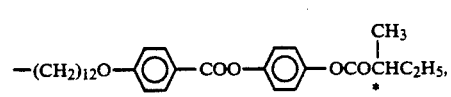

-continued

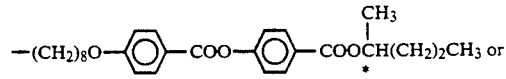
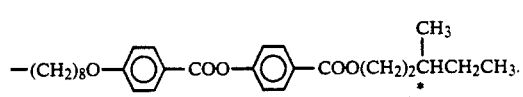

8. The liquid-crystalline copolymer as claimed in claim 1, wherein $R^1$ is

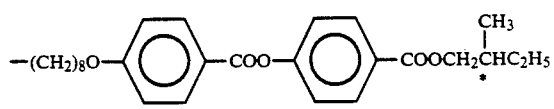

and $R^2$ is

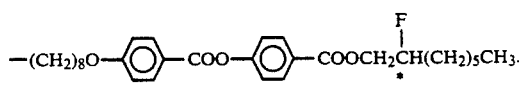

9. The liquid-crystalline copolymer as claimed in claim 1, wherein $R^1$ is

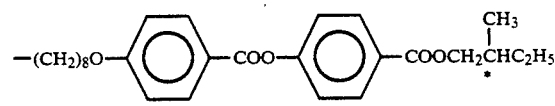

and $R^2$ is

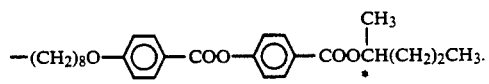

10. The liquid-crystalline copolymer as claiemd in claim 2, wherein r is an integer having a value of from 0 to 2.

11. The liquid-crystalline copolymer as claimed in claim 10, wherein the liquid-crystalline epoxy compound (a) has a helical structure of clockwise twining, the liquid-crystalline epoxy compound (b) has a helical structure having anticlockwise twining, in $R^1$ and $R^2$, $R^3$ independently is

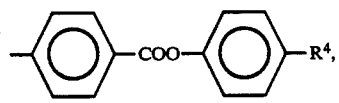
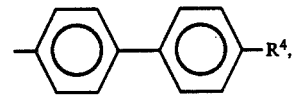
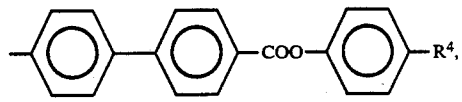

-continued

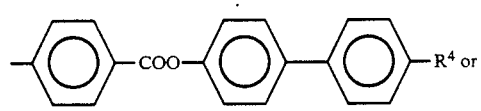

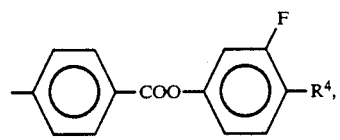

in $R^1$, $R^4$ is

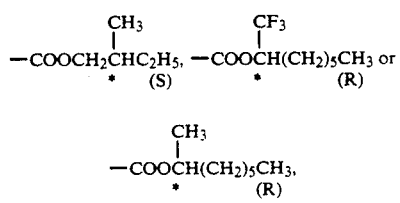

and in $R^2$, $R^4$ is

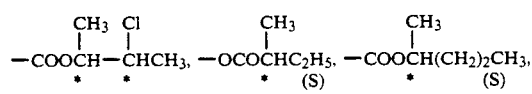

-continued

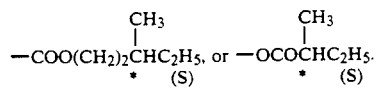

12. The liquid-crystalline copolymer as claimed in claim 11, wherein $R^1$ is

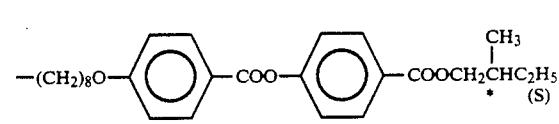

and $R^2$ is

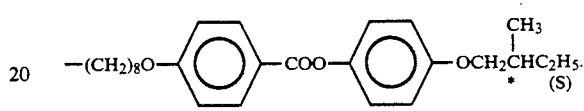

13. The liquid-crystalline copolymer as claimed in claim 12, wherein the molar ratio of the repeating unit (3) to the repeating unit (4) is from 80:20 to 20:80.

14. The liquid-crystalline copolymer as claimed in claim 1, wherein the number average molecular weight of the liquid-crystalline copolymer is from 1,000 to 500,000.

* * * * *